US010426938B2

(12) United States Patent
Locke et al.

(10) Patent No.: US 10,426,938 B2
(45) Date of Patent: Oct. 1, 2019

(54) MEDICAL DRESSING INTERFACE DEVICES, SYSTEMS, AND METHODS

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 409 days.

(21) Appl. No.: 15/198,891

(22) Filed: Jun. 30, 2016

(65) Prior Publication Data
US 2017/0014606 A1 Jan. 19, 2017

Related U.S. Application Data

(60) Provisional application No. 62/192,425, filed on Jul. 14, 2015.

(51) Int. Cl.
*A61M 35/00* (2006.01)
*A61M 1/00* (2006.01)
*A61F 13/00* (2006.01)

(52) U.S. Cl.
CPC ....... *A61M 35/00* (2013.01); *A61F 13/00063* (2013.01); *A61F 13/00068* (2013.01);
(Continued)

(58) Field of Classification Search
CPC .............. A61M 35/00; A61F 13/00063; A61F 2013/00174
See application file for complete search history.

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Tatyana Zalukaeva
*Assistant Examiner* — Gabriella E Burnette

(57) ABSTRACT

An adapter for providing fluid communication with a tissue site may include a base, a conduit housing, a primary port, at least one ancillary port, and at least one port extension. The base may define a mounting plane having a first planar side and a second planar side opposite the first planar side. The conduit housing may be supported by the base and may include a recessed region defining an entry surface. The conduit housing and the recessed region may be positioned on the first planar side with the entry surface facing the first planar side. The primary port may be on the entry surface, and the at least one ancillary port may be on the entry surface. A distal end of the port extension may be positioned on the second planar side in fluid communication with the ancillary port. Other devices, systems, and methods are disclosed.

31 Claims, 13 Drawing Sheets

(52) U.S. Cl.
CPC ........ *A61M 1/0086* (2014.02); *A61M 1/0088* (2013.01); *A61F 2013/00174* (2013.01); *A61M 2205/3344* (2013.01)

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,651,484 B2 * | 1/2010 | Heaton ............... A61M 1/0088 604/313 |
| 8,870,837 B2 * | 10/2014 | Locke ................. A61M 1/0086 604/317 |
| 9,744,278 B2 * | 8/2017 | Locke ................. A61M 1/0088 |
| 10,092,454 B2 * | 10/2018 | Locke ................. A61M 1/0088 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2013/0030394 A1 * | 1/2013 | Locke ................. A61M 1/0088 604/319 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

(56) References Cited

OTHER PUBLICATIONS

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

MEDICAL DRESSING INTERFACE DEVICES, SYSTEMS, AND METHODS

RELATED APPLICATION

This application claims the benefit, under 35 USC 119(e), of the filing of U.S. Provisional Patent Application No. 62/192,425, entitled "Medical Dressing Interface Devices, Systems, and Methods," filed Jul. 14, 2015, which is incorporated herein by reference for all purposes.

TECHNICAL FIELD

This disclosure relates generally to tissue treatment systems, and more particularly, but without limitation, to medical dressing interface devices, systems, and methods that may be suitable for use with reduced-pressure therapy and instillation therapy.

BACKGROUND

Clinical studies and practice have shown that reducing pressure in proximity to a tissue site can augment and accelerate growth of new tissue at the tissue site. The applications of this phenomenon are numerous, but have been proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "reduced-pressure therapy." However, such treatment may also be known by other names including "negative-pressure therapy," "negative-pressure wound therapy," "vacuum therapy," "vacuum-assisted closure," and "topical negative-pressure," for example. Reduced-pressure therapy may provide a number of benefits, including migration of epithelial and subcutaneous tissues, improved blood flow, and micro-deformation of tissue at a tissue site. Together, these benefits can increase development of granulation tissue and reduce healing times.

Cleansing a tissue site can also be highly beneficial for new tissue growth. For example, a tissue site can be washed with a stream of liquid solution, or a cavity can be washed using a liquid solution for therapeutic purposes. Further, fluid may be introduced to a tissue site and left at the tissue site for a prescribed period of time before removing the fluid. These practices may be referred to as "irrigation," "lavage," and "instillation." Instillation of topical treatment solutions over a wound bed or other tissue site can be combined with reduced-pressure therapy to further promote healing and tissue growth by loosening soluble contaminants and removing infectious material. As a result, soluble bacterial burden can be decreased, contaminants removed, and the tissue site cleansed.

Cost and complexity can limit the application of reduced-pressure therapy and instillation therapy systems. Development and operation of therapy systems, components, and processes may benefit manufacturers, healthcare providers, and patients.

SUMMARY

New and useful devices, systems, and methods that may be suitable for use with reduced-pressure therapy and instillation therapy are set forth in the appended claims. For example, in some illustrative embodiments, an adapter for providing fluid communication with a distribution manifold at a tissue site may include a base, a conduit housing, a primary port, at least one ancillary port, and at least one port extension. The base may define a mounting plane having a first planar side and a second planar side opposite the first planar side. Further, the base may include a mounting surface coplanar with the first planar side and facing the first planar side. The conduit housing may be supported by the base and may include a recessed region defining an entry surface. The conduit housing and the recessed region may be positioned on the first planar side with the entry surface facing the first planar side. The primary port may be on the entry surface, and the at least one ancillary port may be on the entry surface. The at least one port extension may include a proximal end, a distal end, and a bore between the proximal end and the distal end. The distal end of the port extension may be positioned on the second planar side in fluid communication with the ancillary port through the bore.

In some illustrative embodiments, a system for treating a tissue site may include a distribution manifold, an adapter, and a reduced pressure source. The distribution manifold may include a tissue-facing side adapted to face the tissue site, and an outward-facing side opposite the tissue-facing side. The adapter may be for providing fluid communication with the distribution manifold. The adapter may include a base, a conduit housing, a primary port, at least one ancillary port, and at least one port extension. The base may include a mounting surface adapted to be positioned on the distribution manifold. The conduit housing may be supported by the base and may include a recessed region defining an entry surface. The entry surface may be adapted to be positioned facing the distribution manifold. The primary port may be positioned on the entry surface, and the at least one ancillary port may be positioned on the entry surface. The at least one port extension may include a proximal end, a distal end, and a bore between the proximal end and the distal end. The distal end of the port extension may be adapted to extend into the distribution manifold when the mounting surface is positioned on the distribution manifold. The distal end of the port extension may also be in fluid communication with the ancillary port through the bore. The reduced pressure source may be adapted to be positioned in fluid communication with the primary port through the conduit housing In some illustrative embodiments, a method for evaluating a service life of a distribution manifold for treating a tissue site may include positioning the distribution manifold on a surface of the tissue site. The distribution manifold may include a tissue-facing side facing the tissue site, and an outward-facing side opposite the tissue-facing side. Further, the method may include positioning an adapter on the distribution manifold. The adapter may include a conduit housing, a primary port, a first ancillary port, a second ancillary port, and a port extension. The conduit housing may include a recessed region defining an entry surface. The entry surface may face the outward-facing side of the distribution manifold. The primary port may be on the entry surface. Further, the first ancillary port and the second ancillary port may be on the entry surface. The port extension may include a proximal end, a distal end, and a bore between the proximal end and the distal end. The distal end of the port extension may be in fluid communication with the first ancillary port. Further, the method may include inserting the distal end of the port extension into the distribution manifold, and applying reduced pressure to the distribution manifold through the primary port. Further, the method may include measuring a first pressure between the surface of the tissue site and the tissue-facing side of the distribution manifold through the first ancillary port and the distal end of the port extension. Further, the method may include measuring a second pressure at the outward-facing side of the distribution manifold through the second ancillary port. Further, the method may include calculating a difference between the first pressure and the second pressure to provide a differential pressure.

In some illustrative embodiments, a method for treating a tissue site may include providing a distribution manifold. The distribution manifold may include a tissue-facing side for facing the tissue site, and an outward-facing side opposite the tissue-facing side. Further, the method may include applying reduced pressure to the outward-facing side of the distribution manifold. Further, the method may include measuring a first pressure at the tissue-facing side of the distribution manifold. Further, the method may include measuring a second pressure at the outward-facing side of the distribution manifold. Further, the method may include calculating a difference between the first pressure and the second pressure to provide a differential pressure.

In some illustrative embodiments, a method for measuring and controlling pressure at a tissue site may include positioning a distribution manifold adjacent a surface of the tissue site. The distribution manifold may include a tissue-facing side facing the tissue site, and an outward-facing side opposite the tissue-facing side. Further, the method may include positioning an adapter adjacent the distribution manifold. The adapter may include a conduit housing, a primary port, a first ancillary port, a second ancillary port, a first port extension, and a second port extension. The conduit housing may include a recessed region defining an entry surface. The entry surface may face the outward-facing side of the distribution manifold. The primary port may be on the entry surface. Further, the first ancillary port and the second ancillary port may be on the entry surface. The first port extension and the second port extension may each include a proximal end, a distal end, and a bore between the proximal end and the distal end. The distal end of the first port extension may be in fluid communication with the first ancillary port, and the distal end of the second port extension may be in fluid communication with the second ancillary port. Further, the method may include inserting the distal end of the first port extension and the distal end of the second port extension into the distribution manifold. Further, the method may include applying reduced pressure from a reduced pressure source to the distribution manifold through the primary port. Further, the method may include measuring a first pressure between the tissue-facing side of the distribution manifold and the surface of the tissue site through the first port extension. Further, the method may include measuring a second pressure between the tissue-facing side of the distribution manifold and the surface of the tissue site through the second port extension. Further, the method may include controlling the reduced pressure from the reduced pressure source according to the first pressure and the second pressure.

In some illustrative embodiments, a method for measuring and controlling pressure at a tissue site may include positioning a distribution manifold adjacent a surface of the tissue site. The distribution manifold may include a tissue-facing side facing the tissue site, and an outward-facing side opposite the tissue-facing side. Further, the method may include applying reduced pressure from a reduced pressure source to the distribution manifold. Further, the method may include measuring a first pressure between the surface of the tissue site and the tissue-facing side of the distribution manifold. Further, the method may include measuring a second pressure between the surface of the tissue site and the tissue-facing side of the distribution manifold. Further, the method may include controlling the reduced pressure from the reduced pressure source according to the first pressure and the second pressure.

In some illustrative embodiments, a method for instilling fluid at a tissue site may include positioning a distribution manifold adjacent a surface of the tissue site. The distribution manifold may include a tissue-facing side facing the tissue site, and an outward-facing side opposite the tissue-facing side. Further, the method may include positioning an adapter adjacent the distribution manifold. The adapter may include a conduit housing, a primary port, at least one ancillary port, and at least one port extension. The conduit housing may include a recessed region defining an entry surface. The entry surface may face the outward-facing side of the distribution manifold. The primary port may be on the entry surface, and the at least one ancillary port may be on the entry surface. The at least one port extension may include a proximal end, a distal end, and a bore between the proximal end and the distal end. The distal end of the port extension may be in fluid communication with the ancillary port through the bore. Further, the method may include inserting the distal end of the port extension into the distribution manifold, and delivering fluid to the surface of the tissue site through the ancillary port and the distal end of the port extension.

In some illustrative embodiments, a method for instilling fluid at a tissue site may include positioning a distribution manifold adjacent a surface of the tissue site. The distribution manifold may include a tissue-facing side facing the tissue site, and an outward-facing side opposite the tissue-facing side. Further, the method may include delivering fluid directly between the surface of the tissue site and the tissue-facing side of the distribution manifold.

In some illustrative embodiments, an adapter for providing fluid communication with a distribution manifold at a tissue site may include a base, a housing, a primary port, at least one ancillary port, and at least one fluid pathway. The base may include a mounting surface. The housing may be supported by the base. The housing may include an opening extending inbound of the mounting surface of the base. The primary port and the at least one ancillary port may be positioned in the opening. The at least one ancillary fluid pathway may extend from the at least one ancillary port outbound of the mounting surface of the base.

In some embodiments, the at least one ancillary fluid pathway may extend beyond the mounting surface of the base. Further, in some embodiments, the primary port and the at least one ancillary port may be positioned inbound of the mounting surface of the base and on an interior surface of the opening. Further, in some embodiments, the primary port may be spaced apart from the at least one ancillary port such that the at least one ancillary port is positioned closer to the mounting surface of the base than the primary port. Further, in some embodiments, the at least one ancillary fluid pathway may have a proximal end and a distal end. The proximal end of the at least one ancillary fluid pathway may be positioned inbound of the mounting surface of the base. The distal end of the at least one ancillary fluid pathway may be positioned outbound of the mounting surface of the base. Further, in some embodiments, the opening of the housing may have an apex positioned inbound of the mounting surface of the base, and the primary port may be positioned at the apex. In some embodiments, the at least one ancillary fluid pathway may include an auxiliary tube. The auxiliary tube may include a proximal end, a distal end, and a bore between the proximal end and the distal end. The distal end of the auxiliary tube may be positioned outbound pf the mounting surface of the base and in fluid communication with the ancillary port through the bore.

In some illustrative embodiments, a method for treating a tissue site may include positioning a distribution manifold on a surface of the tissue site. The distribution manifold may include a tissue-facing side facing the tissue site and an outward-facing side opposite the tissue-facing side. Further, the method may include providing an adapter. The adapter may include a conduit housing, a primary port, an ancillary port, and an ancillary fluid pathway. The conduit housing may include a recessed region defining an entry surface. The primary port and the ancillary port may be positioned on the entry surface. The ancillary fluid pathway may be disposed through the conduit housing and extend outward from the conduit housing. Further, the method may include positioning the adapter on the distribution manifold such that the ancillary port is positioned on the outward-facing side of the distribution manifold and the ancillary fluid pathway extends into the distribution manifold.

In some embodiments, the entry surface may face the outward-facing side of the distribution manifold when the adapter is positioned on the distribution manifold. Further, in some embodiments, the method may include applying reduced pressure to the distribution manifold through the primary port; measuring a first pressure through the ancillary fluid pathway; measuring a second pressure through the ancillary port; and calculating a difference between the first pressure and the second pressure to provide a differential pressure. In some embodiments, the first pressure may be measured between the surface of the tissue site and the tissue-facing side of the distribution manifold. Further, in some embodiments, the second pressure may be measured at the outward-facing side of the distribution manifold. Further, in some embodiment, the method may include changing the distribution manifold if the differential pressure is greater than 15 mm Hg.

Objectives, advantages, and a preferred mode of making and using the claimed subject matter may be understood best by reference to the accompanying drawings in conjunction with the following detailed description of illustrative embodiments.

DETAILED DESCRIPTION OF EXAMPLE EMBODIMENTS

Figure 1:
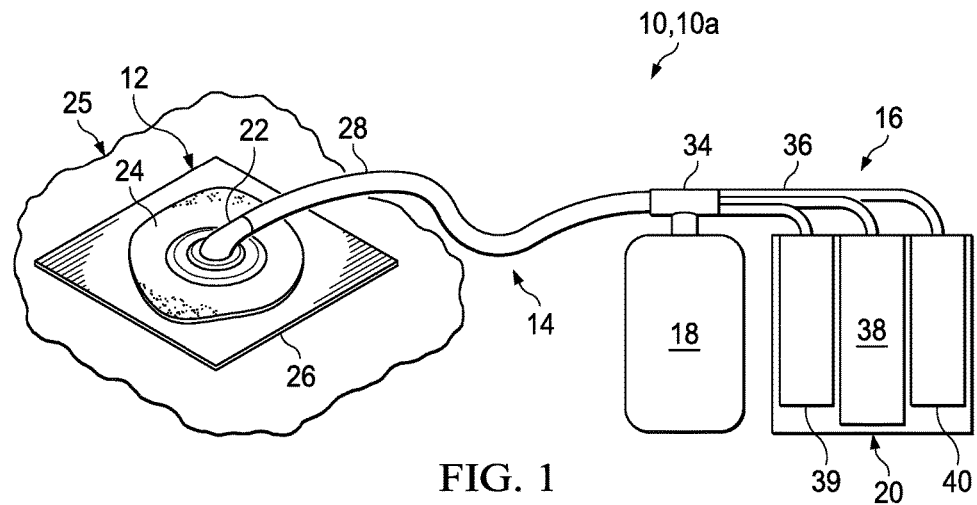
FIG. 1 is a partially schematic, perspective view of a reduced pressure wound treatment (RPWT) system including improvements according to an example embodiment of this disclosure.

The following detailed description of example embodiments makes reference to the accompanying drawings and provides sufficient information to enable a person skilled in the art to make and use the subject matter set forth in the appended claims. However, the detailed description may omit details known in the art. Other embodiments may be possible, and structural, mechanical, electrical, and chemical modifications may be made to the example embodiments herein without departing from the scope of this disclosure as defined by the appended claims. Therefore, the following detailed description is illustrative and non-limiting.

Provided are improvements to reduced-pressure therapy and instillation therapy systems that may include an adapter to improve operational reliability. For example, the adapter may be configured to prevent or reduce instances of unintentional liquid ingress into measurement lumens or sensing lumens associated with a therapy system. Further, the adapter may be configured to position measurement lumens, sensing lumens, or instillation lumens, which may all be referred to as ancillary lumens, closer to a point of interest at a tissue site, such as a surface of the tissue site. The lumens may be separate or isolated from communicating with one another between the point of interest and components, such as, without limitation, a sensor, an instillation reservoir, or a reduced pressure source. Such a configuration may increase the accuracy of pressure measurements at the tissue site, and provide for efficient use of instillation fluid. Improvements to reduced-pressure therapy and instillation therapy methodologies are also provided.

Herein, the term "tissue site" may broadly refer to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. Although reference may be made to a wound, the devices, systems, and methodologies herein are provided without limitation to any particular type of tissue site.

Further, the term "negative pressure" may refer to a pressure less than a local ambient pressure, such as the ambient pressure external to a sealed therapeutic environment that may be provided by a therapy system, or portion of a therapy system, such as a dressing. The local ambient pressure may also be the atmospheric pressure at the location of a tissue site. The pressure may also be less than a hydrostatic pressure associated with tissue at the tissue site. Unless otherwise indicated, values of pressure stated herein are gauge pressures. Further, references to increases in negative pressure may refer to a decrease in absolute pressure, while decreases in negative pressure may refer to an increase in absolute pressure. While the amount and nature of negative pressure applied to a tissue site may vary according to therapeutic requirements, the pressure is generally a low vacuum, also commonly referred to as a rough vacuum, that may be between −5 mm Hg (−667 Pa) and −500 mm Hg (−66.7 kPa). Common therapeutic ranges may be between −75 mm Hg (−9.9 kPa) and −300 mm Hg (−39.9 kPa).

Figure 16:
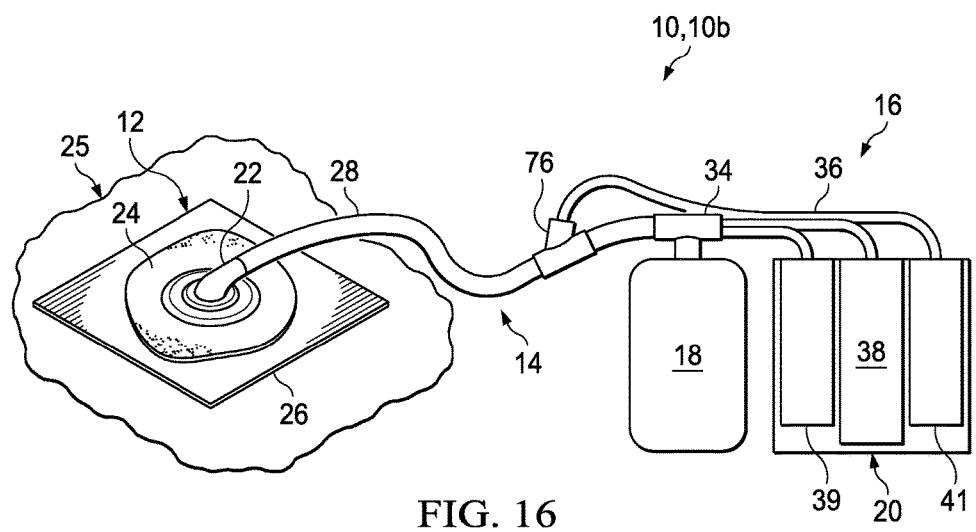
FIG. 16 is a partially schematic, perspective view of a reduced pressure wound treatment (RPWT) system including improvements according to another example embodiment of this disclosure.

Reference is made first to FIG. 1 for a general description of components that may be included in a reduced pressure wound treatment (RPWT) system according to an example embodiment of this disclosure. In some embodiments, a RPWT system 10 may include a wound dressing 12, a delivery tube 14, and a fluid containment and instrumentation assembly 16. The fluid containment and instrumentation assembly 16 may include a fluid container 18 and instrumentation components 20. Further, the RPWT system 10 may include an adapter 22 that may be in fluid communication between the wound dressing 12 and the delivery tube 14. The delivery tube 14 may be in fluid communication between the adapter 22 and the fluid containment and instrumentation assembly 16. In some embodiments, the adapter 22 may be included as part of the wound dressing 12. The RPWT system 10 is shown in FIG. 1 in one embodiment as a RPWT system 10a. FIG. 16 discloses another embodiment of the RPWT system 10, referred to as a RPWT system 10b. References herein to the RPWT system 10 may refer to elements or components that may be associated with both the RPWT system 10a and the RPWT system 10b. Further, like reference numerals herein and among the drawing figures may refer to like elements and components.

The wound dressing 12 may include a distribution manifold 24, such as a porous pad or granular foam, and a cover or drape 26 that may secure the distribution manifold 24 at a tissue site 25. The adapter 22 may provide fluid communication with the distribution manifold 24, and may be positioned on the distribution manifold 24 and adhered thereto by, for example, an adhesive positioned on the adapter 22, the wound drape 26, or a separate adhesive drape associated with the adapter 22.

The fluid container 18 may be representative of a container, canister, pouch, or other storage component suitable for managing exudates and other fluids withdrawn from the tissue site 25. In some embodiments, the fluid container 18 may be a rigid container suitable for collecting, storing, and disposing of fluids.

The distribution manifold 24 may include any substance or structure providing a plurality of pathways adapted to collect or distribute fluid across a tissue site, such as the tissue site 25, under pressure. For example, the distribution manifold 24 may be adapted to receive negative pressure from a source and to distribute negative pressure through multiple apertures across the tissue site 25, which may have the effect of collecting fluid from across the tissue site 25 and drawing the fluid toward the source. In some embodiments, the fluid path may be reversed or a secondary fluid path may be provided to facilitate delivering fluid across the tissue site 25.

In some embodiments, the pathways of the distribution manifold 24 may be interconnected to improve distribution or collection of fluids across the tissue site 25. Further, in some embodiments, the distribution manifold 24 may be a porous foam material having interconnected cells or pores. For example, cellular foam, open-cell foam, reticulated foam, porous tissue collections, and other porous material such as gauze or felted mat generally include pores, edges, or walls adapted to form interconnected fluid channels. Liquids, gels, and other foams may also include or be cured to include apertures and fluid pathways. In some embodiments, the distribution manifold 24 may additionally or alternatively comprise projections that form interconnected fluid pathways. For example, the distribution manifold 24 may be molded to provide surface projections that define interconnected fluid pathways.

In one non-limiting example, the distribution manifold 24 may be an open-cell, reticulated polyurethane foam such as GranuFoam® dressing or VeraFlo® foam, both available from Kinetic Concepts, Inc. of San Antonio, Tex. Further, in some embodiments, the distribution manifold 24 may be either hydrophobic or hydrophilic. In an example in which the distribution manifold 24 may be hydrophilic, the distribution manifold 24 may also wick fluid away from the tissue site 25, while continuing to distribute negative pressure to the tissue site 25. The wicking properties of the distribution manifold 24 may draw fluid away from the tissue site 25 by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The drape 26 may be, for example, an elastomeric film or membrane that can provide a seal adequate to maintain a negative pressure at the tissue site 25 for a given negative-pressure source. The drape 26 may have a high moisture-vapor transmission rate (MVTR) in some embodiments. For example, the MVTR may be at least 300 g/m^2 per twenty-four hours in some embodiments. In some example embodiments, the drape 26 may be a polymer drape, such as a polyurethane film, that may be permeable to water vapor but impermeable to liquid. In such an embodiment, the drape 26 may have a thickness in the range of 25-50 microns. For permeable materials, the permeability generally should be low enough that a desired negative pressure may be maintained.

The delivery tube 14 may include one or more tubing sections 28 which, as an assembled structure, may provide a continuous conduit between the adapter 22 and a container connector 34 that may be positioned on the fluid container 18. Liquid and exudates drawn by the RPWT system 10 may be removed from the delivery tube 14 at the container connector 34 and be retained within the fluid container 18. Sections of additional tubing in the form of instrumentation tubing 36 may extend from the container connector 34 to the instrumentation components 20.

As shown in FIG. 1, in some embodiments, the instrumentation components 20 may include a reduced pressure source 38, a pressure sensor such as a first pressure sensor 39, and another pressure sensor such as a second pressure sensor 40. In other embodiments, as shown in FIG. 16 and described further below, the instrumentation components 20 may include the reduced pressure source 38, the pressure sensor 39, and an instillation reservoir 41. Each of the instrumentation components 20 may be individually associated with one isolated conduit, tube, or lumen that may extend from the adapter 22 into the fluid containment and instrumentation assembly 16.

As a non-limiting example, the reduced pressure source 38 may be a reservoir of air at a negative pressure, or a manual or electrically-powered device that can reduce the pressure in a sealed volume, such as a vacuum pump, a suction pump, a wall suction port available at many healthcare facilities, or a micro-pump. The reduced pressure source 38 may be housed within or used in conjunction with other components, such as sensors, processing units, alarm indicators, memory, databases, software, display devices, or user interfaces that may further facilitate therapy. The reduced pressure source may also have one or more supply ports configured to facilitate coupling and de-coupling to one or more distribution components.

Figure 2:
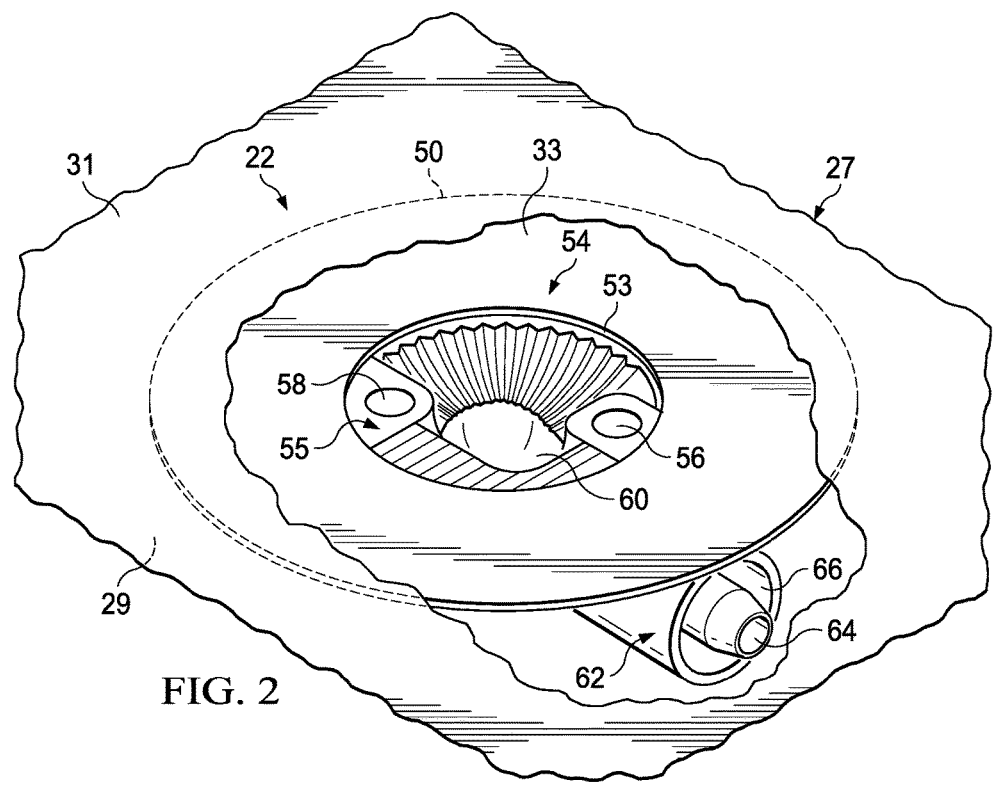
FIG. 2 is a perspective view of an underside or open side of an improved adapter according to an example embodiment of this disclosure.

Reference is now made to FIGS. 2-9 for further description of the reduced pressure adapter 22. FIG. 2 illustrates structural elements within an opening of the adapter 22 that may be adapted to contact the distribution manifold 24 of the wound dressing 12. The adapter 22 may include a base 50 and a housing or a conduit housing 62 that may be supported by or coupled to the base 50.

The base 50 may be adhered to the distribution manifold 24 or to the drape 26 shown in FIG. 1, for example. The base 50 may include a base aperture 53 that may be positioned over the distribution manifold 24. Liquids and gases (collectively referred to as "fluid") may be drawn from the tissue site 25 through the base aperture 53. The adapter 22 may include channel elements positioned near and in fluid communication with the base aperture 53. Described further below, the channel elements may direct and route liquid for drainage while minimizing any interference with other components of the RPWT system 10, such as the instrumentation components 20.

Figure 4:
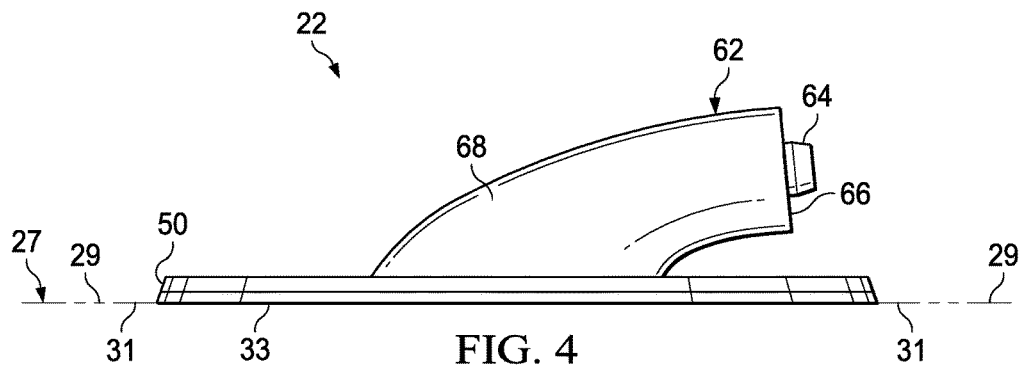
FIG. 4 is a first side view of the improved adapter of FIG. 2.

Further, the base 50 may include a mounting surface 33, and at least a portion of the mounting surface 33 may define a mounting plane 27. In FIGS. 2 and 4, the mounting plane 27 provides a reference or datum point for describing features of the adapter 22 in relation to one another. Thus, the mounting plane 27 is provided for illustration and does not form part of the adapter 22 or otherwise require any component of the adapter 22 to have a planar shape. The mounting plane 27 may have a first proximal side or first planar side 29 and a second distal side or second planar side 31 opposite the first planar side 29. In some embodiments, the first planar side 29 and the second planar side 31 may each refer to a space or territory separated by the mounting plane 27. For example, a first space on the first planar side 29 may be positioned on an opposite side of the mounting plane 27 from a second space on the second planar side 31. The mounting surface 33 of the base 50 may be coplanar with the first planar side 29 and facing the first planar side 29. The mounting surface 33 and the second planar side 31 may be configured to face or to be positioned on the distribution manifold 24.

Continuing with FIG. 2, the conduit housing 62 of the adapter 22 may include an opening or a recessed region 54. The opening or recessed region 54 may define an interior surface or an entry surface 55. The base 50 may be attached to the conduit housing 62 and positioned about the recessed region 54. In some embodiments, the base 50 may partially or completely surround the recessed region 54. The conduit housing 62 and the recessed region 54 may be positioned on the first planar side 29 of the mounting plane 27 with the entry surface 55 facing the first planar side 29. Further, the entry surface 55 may be adapted to face the distribution manifold 24. In some embodiments, the entry surface 55 may be spaced apart from the first planar side 29 of the mounting plane 27.

In some embodiments, the opening or recessed region 54 of the conduit housing 62 may extend in an inbound direction relative to the mounting surface 33 of the base 50. The inbound direction may generally be an opposite direction from a direction the mounting surface 33 is configured to face, such as a facing direction or outbound direction. The facing direction or outbound direction of the mounting surface 33 may be configured to face the tissue site 25 or the distribution manifold 24, for example.

A primary port 60 and at least one ancillary port, such as a first ancillary port 56 and a second ancillary port 58, may be positioned on the entry surface 55. The primary port 60 may be centrally located or positioned at an apex of the recessed region 54, and the ancillary ports 56, 58 may be positioned near opposing edges of the base aperture 53. The apex of the recessed region 54 and the primary port 60 may be spaced apart from the first planar side 29 of the mounting plane 27. In some embodiments, the primary port 60 may be spaced apart from the ancillary ports 56, 58 such that the ancillary ports 56, 58 are positioned closer to the first planar side 29 of the mounting plane 27 than the primary port 60.

In some embodiments, the conduit housing 62 may include a primary conduit (not shown) and a pair of ancillary conduits (not shown) passing through or formed integrally within the conduit housing 62. A first end of the primary conduit may terminate on the entry surface 55 at the primary port 60, and a first end of the ancillary conduits may terminate on the entry surface 55 at the ancillary ports 56, 58, respectively.

Further, in some embodiments, the conduit housing 62 may include a conduit housing aperture 66 that may be adapted to be coupled in fluid communication with the delivery tube 14. A primary lumen interface 64 and at least one ancillary lumen interface, such as ancillary lumen interfaces 48, 49, shown in FIG. 5, may be positioned within the conduit housing aperture 66. In some embodiments, the primary lumen interface 64 may be centrally positioned within the conduit housing aperture 66, and the ancillary lumen interfaces 48, 49 may be positioned about the primary lumen interface 64. A second end of the primary conduit may terminate at the primary lumen interface 64, and a second end of the ancillary conduits may terminate at the ancillary lumen interfaces 48, 49, respectively. Thus, the primary lumen interface 64 may be in fluid communication with the primary port 60 through the primary conduit within the conduit housing 62, and the ancillary lumen interfaces 48, 49 may respectively be in fluid communication with the ancillary ports 56, 58 through the ancillary conduits within the conduit housing 62. Accordingly, the reduced pressure source 38, shown in FIG. 1, may be positioned in fluid communication with the primary port 60 through the conduit housing 62, such as, for example, through the primary lumen interface 64. Similarly, in some embodiments, the first pressure sensor 39 and the second pressure sensor 40, shown in FIG. 1, may be positioned in fluid communication with the ancillary ports 56, 58, respectively, through the conduit housing 62, such as, for example, through the ancillary lumen interfaces 48, 49, respectively. In other embodiments, the pressure sensor 39 and the instillation reservoir 41, shown in FIG. 16, may be positioned in fluid communication with the ancillary ports 56, 58, respectively, through the conduit housing 62, such as, for example, through the ancillary lumen interfaces 48, 49, respectively. Further embodiments are possible.

Figure 3:
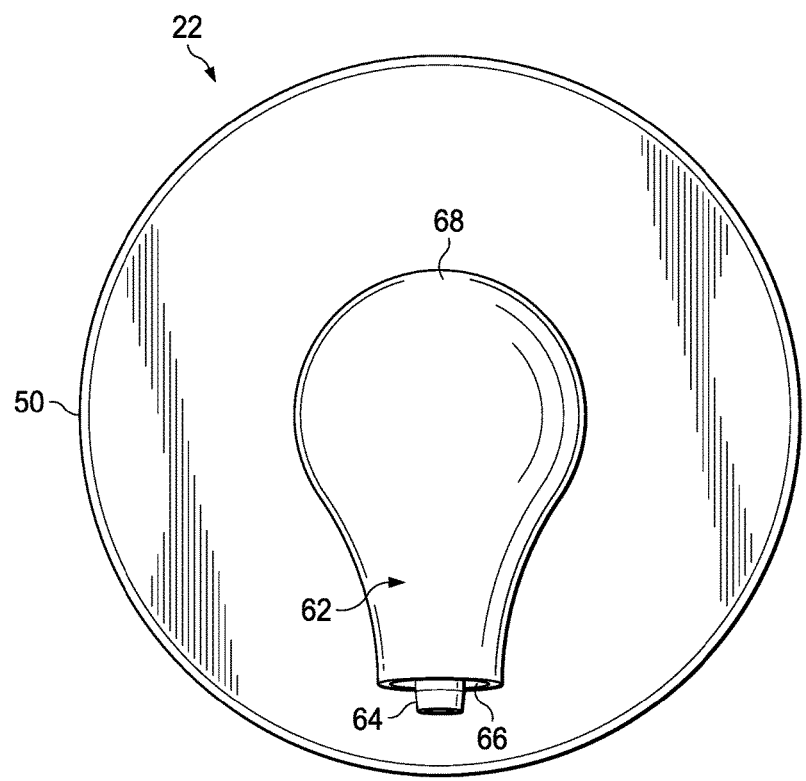
FIG. 3 is a plan view of a topside or closed side of the improved adapter of FIG. 2.

Referring to the topside, plan view of the adapter 22 shown in FIG. 3, the conduit housing 62 may be elbow shaped in some embodiments. However, in other embodiments, the conduit housing 62 may be configured at any desired angle, or may extend perpendicularly from the base 50. Further, as shown in FIG. 3, in some embodiments, the conduit housing 62 may include an elbow region 68, and may be centrally positioned relative to the base 50.

Referring to FIG. 4, in some embodiments, the adapter 22 may have a low profile configuration with the base 50 defining the lateral limits of the adapter 22. As indicated above, the base 50 may be directly adhered to the distribution manifold 24, or may be positioned and adhered using the drape 26 of the wound dressing 12. The adapter 22 may be positioned on distribution manifold 24 such that the base aperture 53 (not seen in this view) of the base 50 is in direct contact with the distribution manifold 24. In the embodiment of FIG. 4, the primary lumen interface 64 may extend outward from the conduit housing 62, and may be surrounded by the conduit housing aperture 66. Conduits may extend through the substrate material of the adapter 22 between the interfaces 48, 49, 64 and the recessed region 54, as described above. The elbow region 68 may redirect fluid flow from the wound dressing 12, which may be positioned beneath the adapter 22, to an angle associated with the primary interface 64 in a manner that may allow the RPWT system 10 to be placed on the wound dressing 12 and be maintained in a low profile configuration close to a surface of the wound dressing 12.

Figure 5:
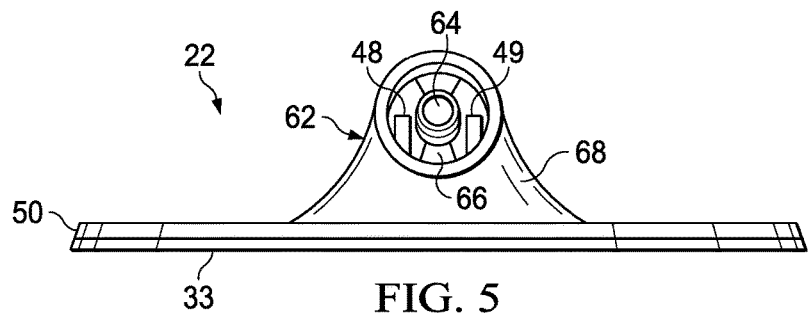
FIG. 5 is an end view of the improved adapter of FIG. 2.

Referring to FIG. 5, another view of the adapter 22 and the configuration of the elbow region 68 and the internal configuration of the conduit housing 62 are shown. The base 50 and the conduit housing aperture 66 are positioned as described above in connection with FIG. 4. The conduit housing 62 may be positioned to receive a section of tubing for connection to components of the RPWT system 10 as described herein.

Continuing with FIG. 5, also depicted are the primary lumen interface 64 and the ancillary lumen interfaces 48 and 49. The ancillary lumen interfaces 48 and 49 may align with corresponding lumens in the delivery tube 14 by, for example, placing a primary lumen 82 in the delivery tube 14 over the primary lumen interface 64 as further described in connection with FIGS. 13A-14B below.

Figure 6:
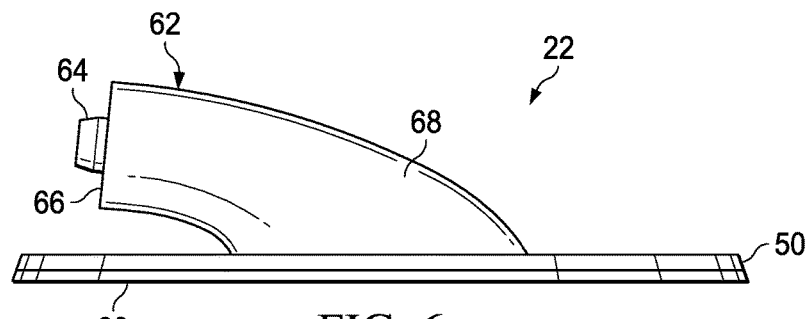
FIG. 6 is a second side view of the improved adapter of FIG. 2.

Referring to FIG. 6, provided is a view of the adapter of FIG. 4 from an opposite side, illustrating the same components previously described in connection with FIG. 4, and the symmetry of the adapter 22 as configured in some embodiments. Unless otherwise indicated, the adaptor 22 may be constructed of any materials capable of providing comfort to the patient while maintaining sufficient rigidity or resilience to maintain the open lumens, conduits, and passageways that are integral to the adapter 22. In some embodiments, the adapter 22 may be formed of flexible materials.

Figure 7:
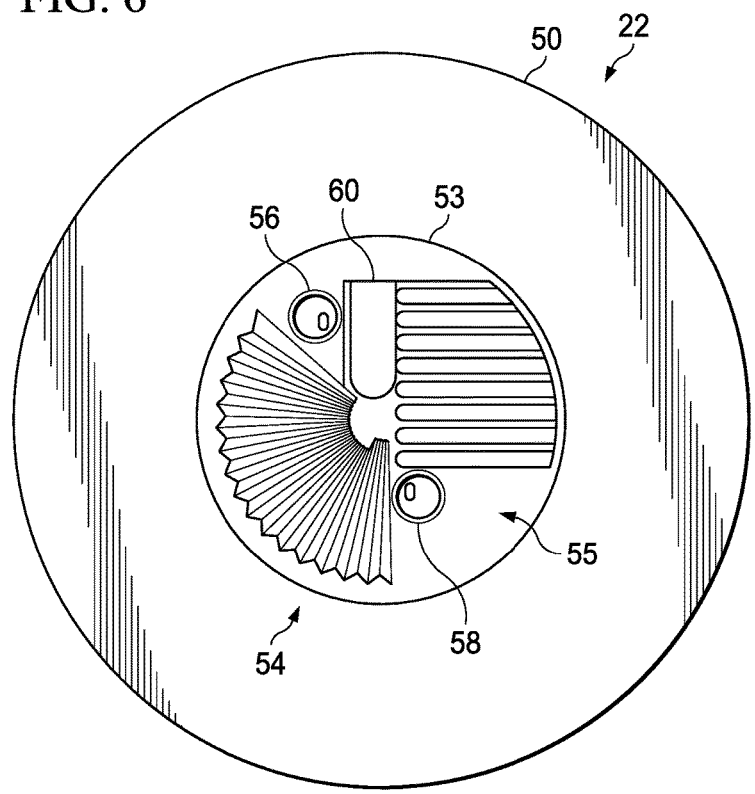
FIG. 7 is a plan view of an underside or open side of the improved adapter of FIG. 2, the underside configured according to an example embodiment of this disclosure.

Referring to FIG. 7, depicted is another view of an embodiment of the adapter 22 to further illustrate the structure and function of elements within the recessed region 54 that may preference liquids and other non-gaseous fluids away from the ancillary ports 56, 58. The base 50 may substantially or entirely surround an edge or perimeter of the recessed region 54. The ancillary ports 56 and 58 are shown positioned as described above. The primary port 60 can be seen centrally located within the recessed region 54. Structures within the recessed region 54 that may serve to conduct liquid into the primary port 60 and the associated primary conduit, and thereby allow the ancillary ports 56, 58, and the associated ancillary conduits to remain unobstructed are described in more detail below with respect to FIG. 9.

Figure 8:
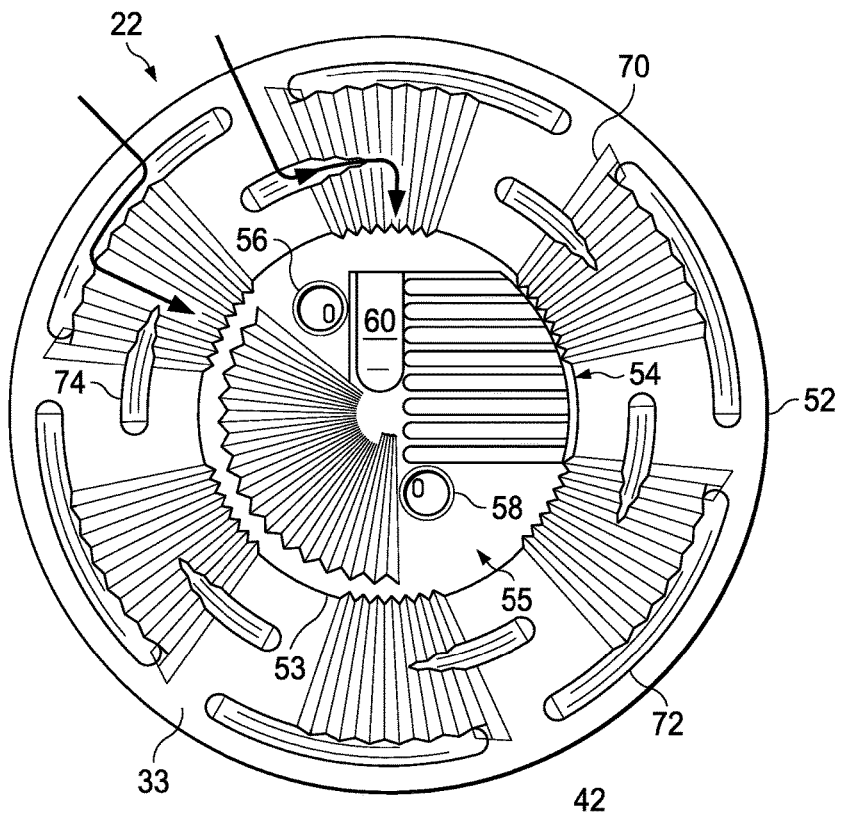
FIG. 8 is a plan view of an underside or open side of the improved adapter of FIG. 2, the underside configured according to another example embodiment of this disclosure.

Referring to FIG. 8, depicted is another embodiment of the base 50, referred to as a base 52, that may be associated with the adapter 22. The base 52 may include base serrated guide channels 70, perimeter collection channels 72, and intermediate collection channels 74. In some embodiments, the base serrated guide channels 70, the perimeter collection channels 72, and the intermediate collection channels 74 may be molded into a mounting surface 33 of the base 52. The base serrated guide channels 70, the perimeter collection channels 72, and the intermediate collection channels 74 as configured in FIG. 8 may direct liquid away from the ancillary ports 56, 58 and into the primary port 60. The base serrated guide channels 70 may be positioned and oriented on the base 52 to directly capture and channel a majority of the liquids being drawn toward or into the adapter 22. The base serrated guide channels 70 may be spaced and radially-oriented to funnel liquids away from the ancillary ports 56, 58 and into the primary port 60. In addition, the perimeter collection channels 72 and the intermediate collection channels 74 may redirect the flow of liquids among portions of the base serrated guide channels 70 and away from the ancillary ports 56, 58. An example of this redirected flow is shown in FIG. 8 with bolded flow indication arrows, where the radial channels 70 or the base serrated guide channels 70 are positioned on the base 52 to direct liquid from a periphery of the base 52 away from the ancillary ports 56, 58. Further, the intermediate collection channels 74 may be positioned on the base 52 to direct liquid into the radial channels 70 or the base serrated guide channels 70.

Figure 9:
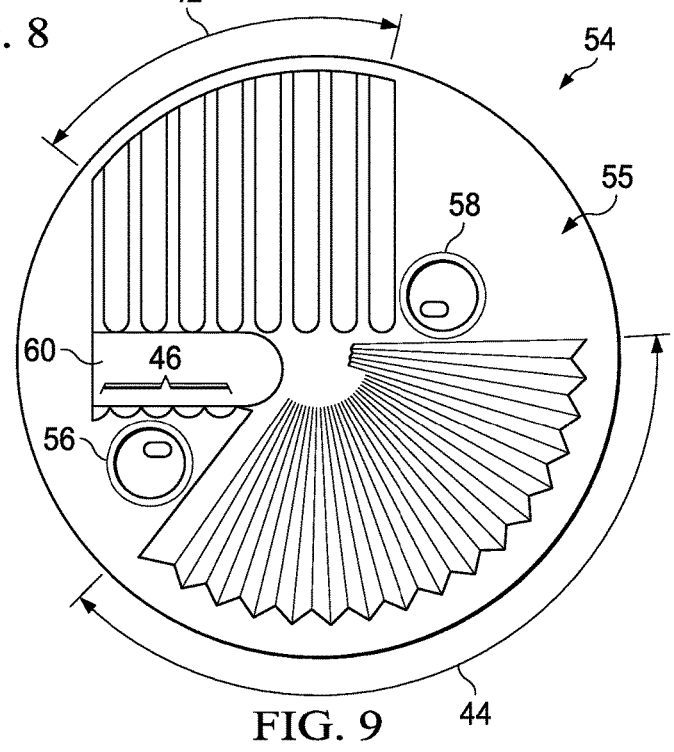
FIG. 9 is a detailed view of an example embodiment of a recessed region of the adapter of FIGS. 7 and 8.

Reference is now made to FIG. 9 for further description of the features and elements that may be contained within the recessed region 54 of the conduit housing 62. These features may be positioned on the entry surface 55 of the recessed region 54, and may be configured to preference liquids and other non-gaseous exudates away from the ancillary ports 56, 58 and into the primary port 60. As shown, in some embodiments, the primary port 60 may be centrally positioned within the recessed region 54, and may extend from this central location to one side of the recessed region 54. Further, the ancillary ports 56 and 58 may be positioned to either side of the primary port 60. As shown, in some embodiments, the ancillary ports 56 and 58 may be circular openings and may have raised circumferential edges.

Various elements shown in the embodiment of FIG. 9 may be positioned to preference liquid into the primary port 60 of the adapter 22. For example, the ancillary ports 56 and 58 may be positioned near a perimeter of the base aperture 53 (shown in FIG. 7) and the recessed region 54, and at a level that may be close to a surface of the distribution manifold 24 when the adapter 22 is positioned thereon. Accordingly, when the adapter 22 is positioned on the wound dressing 12, the ancillary ports 56 and 58 may be in contact, or nearly in contact, with the surface of the distribution manifold 24. Such a configuration may minimize the likelihood of splashed or agitated liquid being directed into the ancillary ports 56 and 58.

Additional elements that may direct liquids into the primary port 60 are structural serrated channels that may be formed on portions of the entry surface 55 of the recessed region 54. A first linear serrated channel section 42 may be positioned in association with an approximately half-circle section of the recessed region 54 that may be associated with the ancillary port 58. The material comprising this section of the recessed region 54 may form a ceiling covering and containing the conduit (not shown) that may extend within the conduit housing 62 between the ancillary port 58 and one of the ancillary lumen interfaces 48, 49 shown in FIG. 5. This ceiling may be configured with an array of serrated channels or striations that may direct liquids that fall upon this surface toward the primary port 60 within the recessed region 54. Any liquids that may fall upon this portion of the entry surface 55 may be channeled directly into the primary port 60, rather than being directed into the ancillary port 58.

Continuing with FIG. 9, a similar configuration may be constructed in an approximately one-third circular radial serrated channel section 44. Insofar as no internal conduit is contained within this section of the recessed region 54, the radial serrated channel section 44 may extend deeper and more directly to the primary port 60. The radial serrated channel section 44 may extend from a perimeter of the recessed region 54 toward an apex of the recessed region 54 that drains into the primary port 60. Further, the radial serrated channel section 44 may extend from the ancillary port 58 radially around approximately a one-third circular portion of the recessed region 54 to the ancillary port 56. Any liquids that fall upon the radial serrated channel section 44 of the recessed region 54 may be directed to the primary port 60, rather than being conducted to either of the ancillary ports 56, 58.

Further, a wall section that supports the ancillary port 56 at the point at which the ancillary port 56 overhangs the primary port 60 may include serrated or striated channels 46. For the orientation shown in FIG. 9, the serrated or striated channels 46 may extend downward from the opening of the ancillary port 56 toward the opening of the primary port 60.

As described above, various elements of the recessed region 54 may be configured to draw liquid from within the recessed region 54 and to direct the liquid toward the primary port 60. Insofar as the configuration of the recessed region 54 provides little or no suction at the ancillary ports 56, 58, the likelihood of obstructions in the form of liquid or material blocking the ancillary lumens 56, 58 may be greatly reduced.

Figure 10:
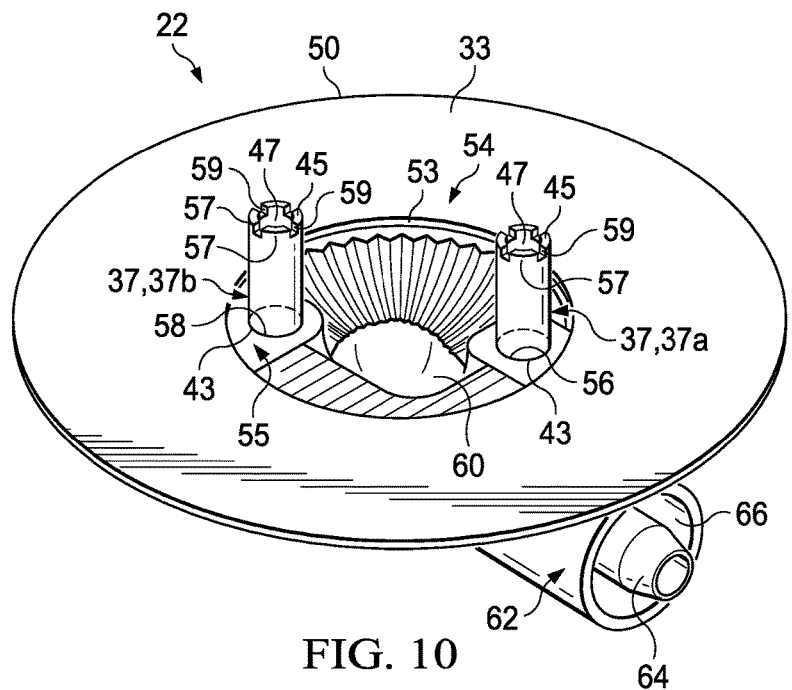
FIG. 10 is a perspective view of an underside or open side of an improved adapter illustrating at least one port extension according to an example embodiment of this disclosure.
Figure 11:
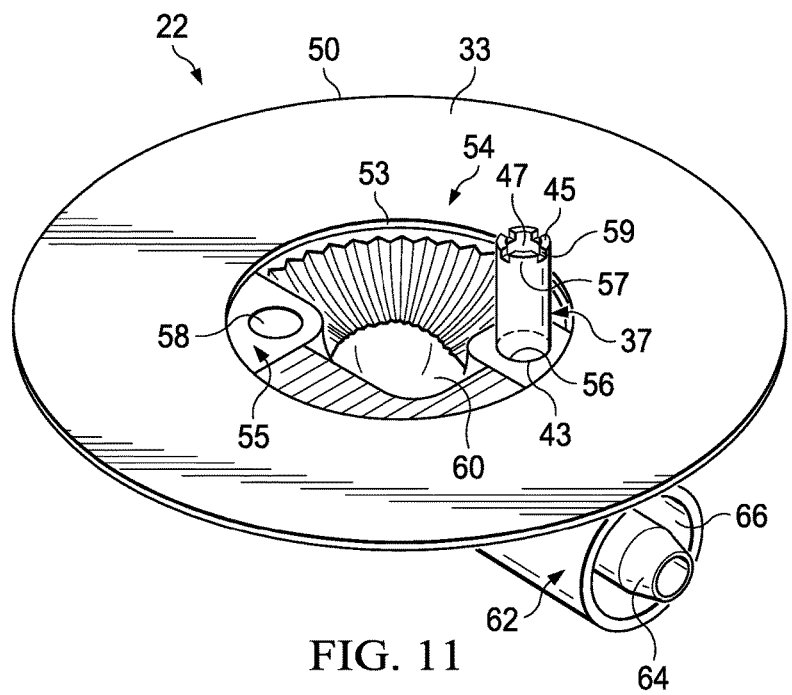
FIG. 11 is a perspective view of an underside or open side of an improved adapter illustrating at least one port extension according to another example embodiment of this disclosure.

Referring to FIGS. 10-11, in some embodiments, the adapter 22 may include at least one auxiliary tube or port extension 37 that may define, form, or provide an ancillary fluid pathway that may extend beyond or outbound of the mounting surface 33 of the base 50. Features described in reference to the port extension 37 herein may be applicable to or interchangeable with the auxiliary tube and the ancillary fluid pathway. Each of the port extensions 37 may include a proximal end 43, a distal end 45, and a bore 47 between the proximal end 43 and the distal end 45. In some embodiments, a length of the port extension 37 between the proximal end 43 and the distal end 45 may be between about 6 millimeters to about 8 millimeters. The proximal end 43 of the port extension 37 may be positioned on or at the first planar side 29 of the mounting plane 27, shown in FIG. 1, in fluid communication with one or more of the ancillary ports 56, 58. In some embodiments, the proximal end 43 of the port extension 37 may be coupled to the entry surface 55 about one or more of the ancillary ports 56, 58.

The distal end 45 of the port extension 37 of FIGS. 10-11 may extend through the mounting plane 27 to the second planar side 31 or beyond the second planar side 31. Thus, the port extension 37 may extend beyond the mounting surface 33 through the mounting plane 27 to the second planar side 31 of the mounting plane 27. Further, the distal end 45 of the port extension 37 may be positioned on the second planar side 31, or beyond the second planar side 31, and in fluid communication with one or more of the ancillary ports 56, 58 through the bore 47. In some embodiments, the bore 47 of the port extension 37 may define an isolated communication passageway between one or more of the ancillary ports 56, 58 and the distal end 45 of the port extension 37. Further, the distal end 45 of the port extension 37 may be spaced apart from the mounting plane 27 on the second planar side 31.

In some embodiments, the port extension 37 may be collapsible or adjustable in a lengthwise direction. For example, in some embodiments, the port extension 37 may be formed of resilient or flexible materials, such as, without limitation a soft polymer or plasticized PVC material. Such materials may permit the port extension 37 to adjust or conform to different shapes and contours at the tissue site 25 while the bore 47 of the port extension 37 remains open or unobstructed. For example, the distal end 45 of the port extension 37 may be moveable in a lengthwise direction along an axis of the bore 47 closer to and farther away from the mounting plane 27 and the coplanar mounting surface 33. Further, in some embodiments, the port extension 37 may carry or be formed with a bellows or corrugation (not shown) configured to permit a wall of the port extension 37 to collapse without restricting fluid communication through the bore 47 of the port extension 37.

In some embodiments, the distal end 45 of the port extension 37 may carry a plurality of castellations 57. In some embodiments, the castellations 57 may be projections extending outward from the distal end 45 of the port extension 37. Further, in some embodiments, the castellations 57 may be disposed about a perimeter of the distal end 45 of the port extension 37. Further, in some embodiments, the castellations 57 may be collapsible in an analogous manner as described above for the port extension 37. Further, in some embodiments, the castellations 57 may be spaced apart from one another about the distal end 45 of the port extension 37. Further, in some embodiments, an opening 59 may be defined between each of the castellations 57. The opening 59 may be in fluid communication with the bore 47 of the port extension 37, for example, to enhance pressure measurement or instillation of fluids through the port extension 37 when the distal end 45 of the port extension 37 is in contact with or in close proximity to a surface of the tissue site 25. Further, in some embodiments, the castellations 57 may have a pitch or spacing of about 0.5 millimeters to about 1.0 millimeters between one another. Such a pitch or spacing may provide a suitable amount of micro-force deformation at the tissue site 25, which may promote healing and the formation of granulation tissue.

In some embodiments, the distal end 45 of the port extension 37 may carry a plurality of apertures or holes (not shown) disposed through a wall of the port extension 37. These apertures or holes may be positioned near the distal end 45 and about a perimeter of the port extension 37. Further, the apertures or holes may be spaced apart from one another about a perimeter or circumference of the port extension 37. Analogous to the opening 59 between the castellations 57, the apertures or holes may be in fluid communication with the bore 47 of the port extension 37 to enhance pressure measurement or instillation of fluids through the port extension 37 when the distal end 45 of the port extension 37 is in contact with or in close proximity to a surface of the tissue site 25.

Referring to FIG. 10, in some embodiments, the at least one port extension 37 may include a first port extension 37a and a second port extension 37b. The proximal end 43 of the first port extension 37a may be coupled about the first ancillary port 56, and the proximal end 43 of the second port extension 37b may be coupled about the second ancillary port 58. The first pressure sensor 39, shown in FIG. 1, may be in fluid communication with the first ancillary port 56 and the first port extension 37a. In some embodiments, the second pressure sensor 40, also shown in FIG. 1, may be in fluid communication with the second ancillary port 58 and the second port extension 37b. In other embodiments, the instillation reservoir 41, shown in FIG. 16, may be in fluid communication with the second ancillary port 58 and the second port extension 37b. Other embodiments are possible.

Referring to FIG. 11, in some embodiments, the port extension 37 may be a single port extension 37 coupled to the entry surface 55 about the first ancillary port 56. For example, the proximal end 43 of the port extension 37 may be coupled to the entry surface 55 about the first ancillary port 56. Further, the distal end 45 of the port extension 37 may extend outward from the entry surface 55 and beyond the mounting surface 33 of the base 50 or the base 52. The second ancillary port 58 may terminate at the entry surface 55. In some embodiments, the first pressure sensor 39, shown in FIG. 1, may be positioned in fluid communication with the first ancillary port 56 and the port extension 37 through the conduit housing 62. Further, the second pressure sensor 40, also shown in FIG. 1, may be positioned in fluid communication with the second ancillary port 58 at the entry surface 55 through the conduit housing 62.

Figure 12A:
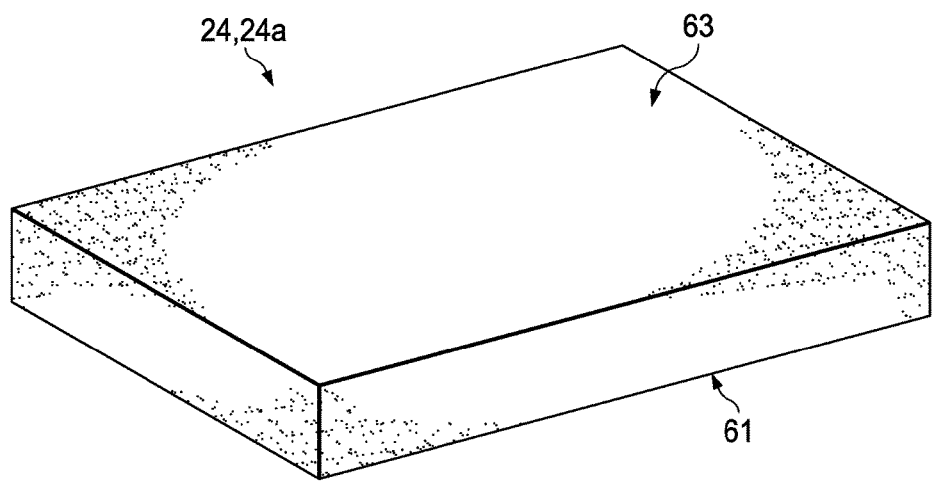
FIG. 12A is a perspective view of an example embodiment of a distribution manifold suitable for use with a RPWT system according to this disclosure.
Figure 12B:
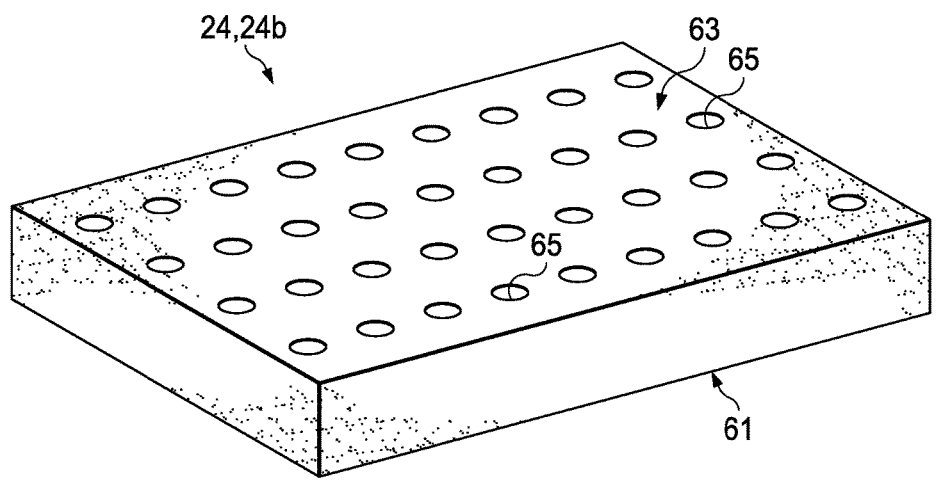
FIG. 12B is a perspective view of another example embodiment of a distribution manifold suitable for use with a RPWT system according to this disclosure.

Referring to FIGS. 12A-12B, the distribution manifold 24 may include additional elements for enhancing the RPWT system 10 and the usability of the adapter 22. For example, the distribution manifold 24 may include a tissue-facing side 61 adapted to face the tissue site 25, shown in FIG. 1, and an outward-facing side 63 opposite the tissue-facing side 61. In some embodiments, the tissue-facing side 61 of the distribution manifold 24 may be adapted to directly or substantially contact the tissue site 25. The drape 26, also shown in FIG. 1, may be adapted to cover the outward-facing side 63 of the distribution manifold 24 at the tissue site 25.

Continuing with FIGS. 12A-12B, with reference to FIGS. 8 and 10-11, the mounting surface 33 of the base 50 or the base 52 may be adapted to be positioned on the outward-facing side 63 of the distribution manifold 24. The distal end 45 of the port extension 37 may be adapted to extend into or to be pressed into the distribution manifold 24 when the mounting surface 33 of the base 50 or the base 52 is positioned on the distribution manifold 24. Further, a length of the port extension 37 may be adapted to extend between the outward-facing side 63 and the tissue-facing side 61 of the distribution manifold 24. In some embodiments, the proximal end 43 of the port extension 37 may be adapted to be positioned at the outward-facing side 63 of the distribution manifold 24, and the distal end 45 of the port extension 37 may be adapted to be positioned at the tissue-facing side 61 of the distribution manifold 24. Further, in some embodiments, the distal end 45 of the port extension 37 may be adapted to contact the tissue site 25.

Referring to FIG. 12A, in some embodiments, the distribution manifold 24 may be a distribution manifold 24a formed, for example, of a sheet or block of any of the materials described above for the distribution manifold 24, which may be cut or otherwise shaped to fit the tissue site 25, shown in FIG. 1. Referring to FIG. 12B, in some embodiments, the distribution manifold 24 may be a distribution manifold 24b including a plurality of port apertures 65 sized, spaced, or otherwise adapted to receive the least one port extension 37. In some embodiments, the port apertures 65 may have a diameter between about 2 millimeters to about 3 millimeters, and a pitch or spacing between about 10 millimeters to about 12 millimeters. The plurality of port apertures 65 may be disposed through a thickness of the distribution manifold 24b, for example, between the outward-facing side 63 and the tissue-facing side 61. In some embodiments, the thickness of the distribution manifold 24a or 24b may be about 30 millimeters.

Reference is now made to FIGS. 13A-14B for further description of the delivery tube 14. In some embodiments, the delivery tube 14 may include the primary lumen 82 and at least one ancillary lumen, such as, for example, a first ancillary lumen 84 and a second ancillary lumen 86. Further, in some embodiments, the delivery tube 14 may be a multi-lumen tube 80, such as, for example, a multi-lumen tube 80a, shown in FIGS. 13A-13B, or a multi-lumen tube 80b, shown in FIGS. 14A-14B. The multi-lumen tubes 80a, 80b may also be used as one or more tubing sections 28 and the instrumentation tubing 36 shown and described in connection with FIGS. 1 and 16. In other embodiments, the delivery tube 14 may be comprised of single or individual lumens that may be routed or coupled separate from one another to various components of the RPWT system 10 described herein.

The primary lumen 82 may be adapted to be in fluid communication between the reduced pressure source 38 and the primary port 60 of the adapter 22 through, for example, the primary conduit within the adapter 22, described above. Further, the at least one ancillary lumen 84, 86 may be adapted to be in fluid communication with one or more of the ancillary ports 56, 58 of the adapter 22 through, for example, the ancillary conduits of the adapter 22, also described above. In some embodiments, the cross-sectional diameter of the primary lumen 82 may be larger or greater than a cross-sectional diameter of the ancillary lumens 84 and 86.

Figure 13A:
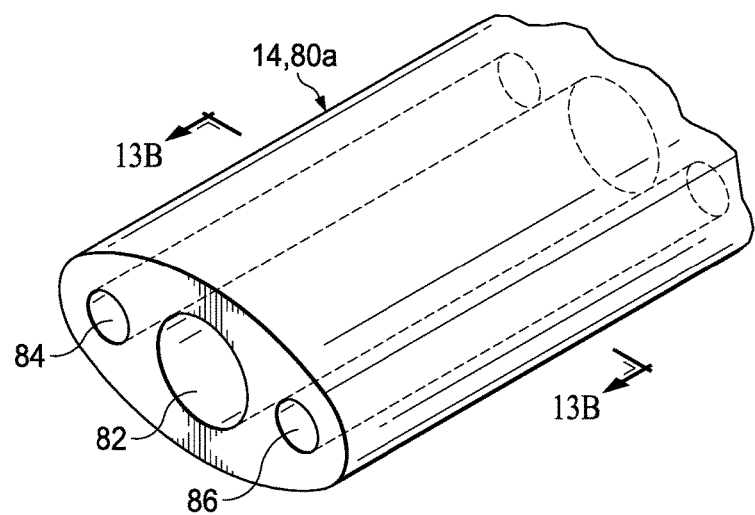
FIG. 13A is a perspective view of an open end of an improved delivery tube according to an example embodiment of this disclosure.
Figure 13B:
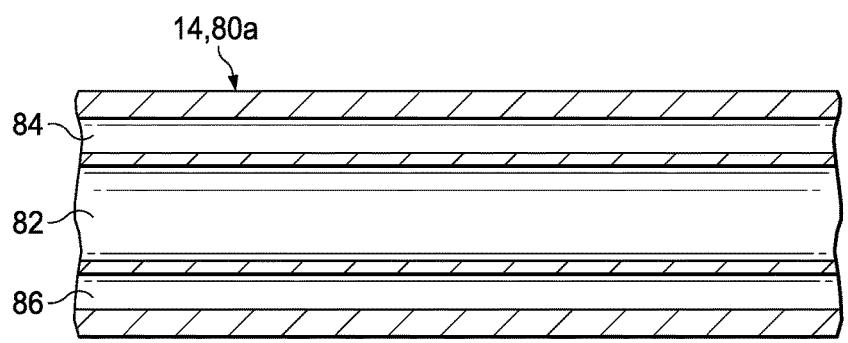
FIG. 13B is a longitudinal cross-sectional view of the improved delivery tube of FIG. 13A.

Referring to FIGS. 13A-13B, in some embodiments, the multi-lumen tube 80a may have an oval cross-section, which may enhance flexibility while precluding the collapse of any of the described lumens. Further, this oval cross-sectional shape may also orient the ancillary lumens 84, 86 in appropriate alignment with the ancillary lumen interfaces 48, 49 of the adapter 22 described above.

Figure 14A:
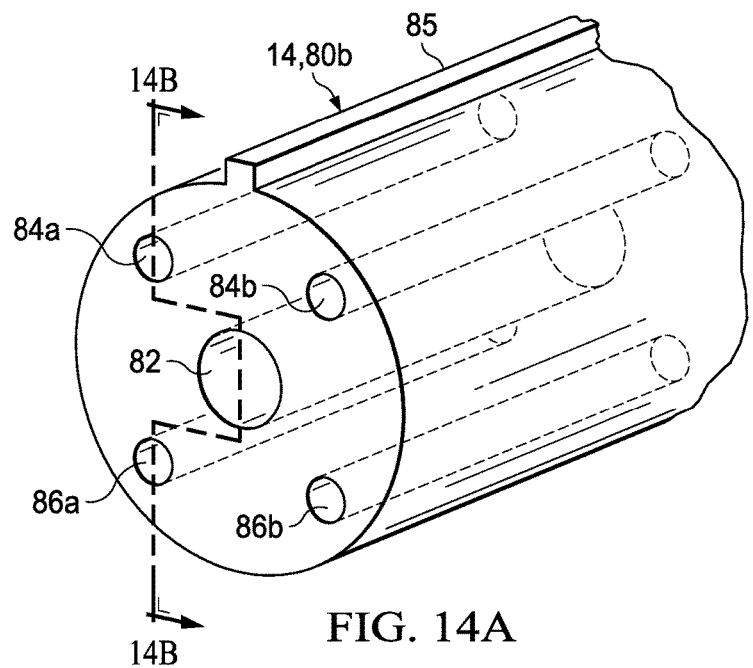
FIG. 14A is a perspective view of an open end of an improved delivery tube according to another example embodiment of this disclosure.
Figure 14B:
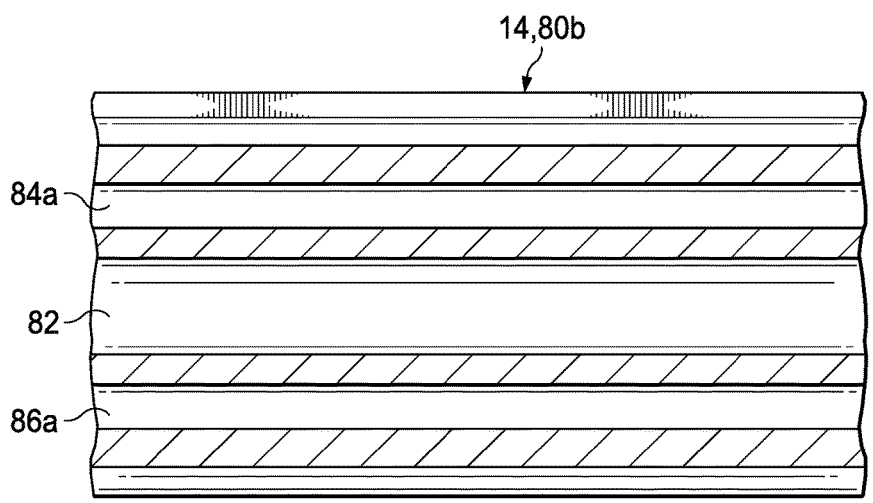
FIG. 14B is a longitudinal cross-sectional view of the improved delivery tube of FIG. 14A.

Referring to FIGS. 14A-14B, in some embodiments, the first ancillary lumen 84 may be a first pair of ancillary lumens 84a, 84b, and the second ancillary lumen 86 may be a second pair of ancillary lumens 86a, 86b. The first pair of ancillary lumens 84a, 84b may be adapted to be in fluid communication with the first ancillary port 56, shown in FIG. 2, and the second pair of ancillary lumens 86a, 86b may be adapted to be in fluid communication with the second ancillary port 58, also shown in FIG. 2. As shown in FIGS. 14A-14B, the primary lumen 82, the first pair of ancillary lumens 84a, 84b, and the second pair of ancillary lumens 86a, 86b may form part of the multi-lumen tube 80b.

In some embodiments, the multi-lumen tube 80b may also include an alignment tab 85 configured or positioned on an exterior of the multi-lumen tube 80b to orient the ancillary lumens 84, 86 in appropriate alignment with the ancillary lumen interfaces 48, 49 of the adapter 22 described above. In other embodiments, a colored line, dots, dashes, or emboss may be used alternatively or in addition to the alignment tab 85. For example, the first pair of ancillary lumens 84a, 84b may be aligned with one of the ancillary lumen interfaces 48, 49, and the second pair of the ancillary lumens 86a, 86b may be aligned with the other of the ancillary lumens interfaces 48, 49. The ancillary lumen interfaces 48, 49 are best viewed in FIG. 5, with reference to FIGS. 14A-14B. In the embodiment shown in FIG. 5, the ancillary lumen interfaces 48, 49 may each include an arcuate passageway shaped to mate with one pair of the ancillary lumens shown in FIGS. 14A-14B, such as the first pair of ancillary lumens 84a, 84b or the second pair of ancillary lumens 86a, 86b. Further, the arcuately shaped passageway of the ancillary lumen interfaces 48, 49, shown in FIG. 5, may also be configured to mate with the ancillary lumens 84, 86 in the multi-lumen tube 80a, shown in FIGS. 13A-13B, with an oval cross-section. Thus, the configuration of the ancillary lumen interfaces 48, 49 provides for the use of both the cross-section of the multi-lumen tube 80a, shown in FIG. 13B, and the cross-section of the multi-lumen tube 80b, shown in FIG. 14B, in the RPWT system 10.

Figure 15:
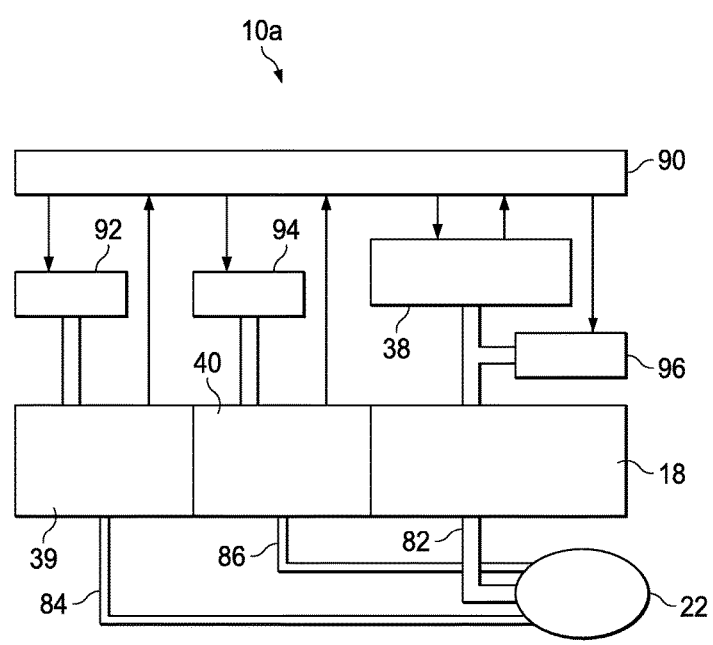
FIG. 15 is a schematic block diagram illustrating a reduced pressure system according to an example embodiment of this disclosure.

FIG. 15 is a schematic diagram illustrating additional details that may be associated with some example embodiments of the RPWT system 10a. FIG. 15 illustrates the reduced pressure source 38, the first pressure sensor 39, and the second pressure sensor 40 in separate fluid communication, for example, through separate lumens or conduits, with the adapter 22 as previously described. The RPWT system 10a may additionally include a controller 90, and solenoid valves 92, 94, and 96. The controller 90 may be configured to receive pressure data from the first pressure sensor 39, the second pressure sensor 40, and the reduced pressure source 38. The controller 90 may also be programmed or configured to monitor pressure at the tissue site 25, shown in FIG. 1, through the pressure data received from the pressure sensors 39, 40. The controller 90 may further be configured to operate the reduced pressure source 38 for supplying reduced pressure to the adapter 22, such as through the previously described primary lumen 82 and primary port 60, according to the pressure data.

In some embodiments, the solenoid valve 92 may be in fluid communication with the first pressure sensor 39, the solenoid valve 94 may be in fluid communication with the second pressure sensor 40, and the solenoid valve 96 may be in fluid communication with the reduced pressure source 38. The controller 90 may be electrically coupled or operable on the solenoid valves 92, 94, and 96, and the reduced pressure source 38. In the RPWT system 10a, the solenoid valves 92, 94, and 96 may be controlled by the controller 90, for example, to regulate pressure at the tissue site 25, and to clear blockages.

For example, in instances where liquid or other non-gaseous substance enters one of the ancillary lumens 84, 86, a blockage may be created, causing a delay in a pressure change response time of the ancillary lumen having the blockage versus the ancillary lumen free of the blockage. The delay may increase as the blockage increases in severity. When a delay is detected, the RPWT system 10a may control the pressure at the tissue site 25 according to the pressure data received from the ancillary lumen free of the blockage. Further, the RPWT system 10a may attempt to clear the blockage by opening a corresponding solenoid valve 92, 94 to atmosphere. If the RPWT system 10a is not successful in clearing the blockage, the RPWT system 10a may ignore any pressure data received from the ancillary lumen with the blockage, and operate based on the pressure data received from the ancillary lumen free of the blockage.

Referring to FIG. 16, provided is another embodiment of the RPWT system 10, referred to as the RPWT system 10b. The instrumentation components 20 of the RPWT system 10b may include the reduced pressure source 38, the pressure sensor 39, and the instillation reservoir 41. A split connector 76 may be optionally employed with the RPWT system 10b to couple the wound dressing 12 in fluid communication with the instillation reservoir 41. The instillation reservoir 41 may be representative of a container, canister, pouch, bag, or other storage component suitable for holding a liquid and for providing a solution for instillation therapy. The instillation reservoir 41 may be positioned in fluid communication with at least one of the ancillary ports 56, 58 through the conduit housing 62. Compositions of instillation solution may vary according to a prescribed therapy, but examples of suitable solutions may include hypochlorite-based solutions, silver nitrate (0.5%), sulfur-based solutions, biguanides, cationic solutions, and isotonic solutions. Like reference numerals appearing in FIG. 16 and in other figures may have analogous structure and functionality as previously described components, and thus, will not be further described.

Figure 17:
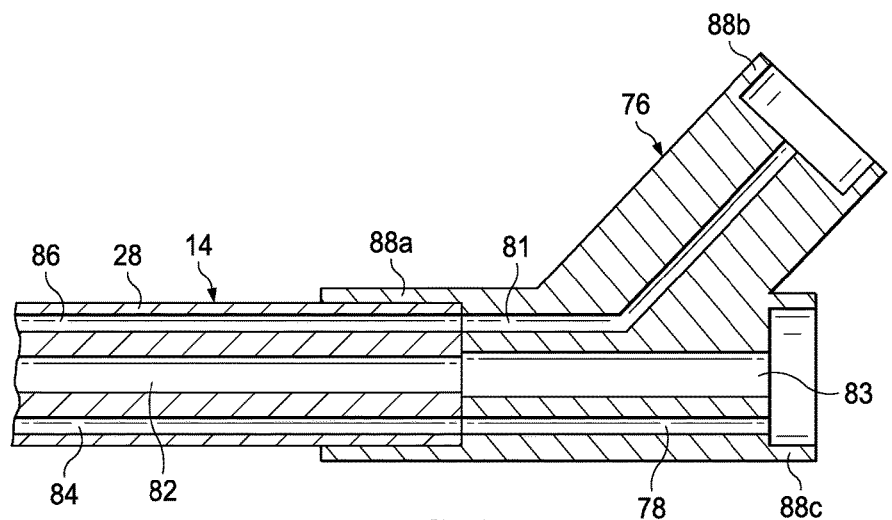
FIG. 17 is a cut-away view of a split connector coupled to a portion of a delivery tube according to an example embodiment of this disclosure.

Referring to FIG. 17, the split connector 76 may be configured to separate out at least one of the ancillary lumens 84, 86 associated with the delivery tube 14 when the delivery tube 14 is configured as a multi-lumen tube, such as the multi-lumen tube 80a, 80b. A tubing section 28 of the delivery tube 14 is shown in FIG. 17 mated to a connector port 88a of the split connector 76 for purposes of illustration. In some embodiments, one of the ancillary lumens 84, 86, such as the second ancillary lumen 86, may be coupled in fluid communication with the instillation reservoir 41, shown in FIG. 16, through the split connector 76. For example, the split connector 76 may include a first ancillary passageway 78, a second ancillary passageway 81, and a primary passageway 83. As shown in FIG. 17, the first ancillary lumen 84 may be in fluid communication with the first ancillary passageway 78, the second ancillary lumen 86 may be in fluid communication with the second ancillary passageway 81, and the primary lumen 82 may be in fluid communication with the primary passageway 83. In some embodiments, the first ancillary passageway 78 may be adapted to be in fluid communication with the first pair of ancillary lumens 84a, 84b, shown in FIG. 14A, and the second ancillary passageway 81 may be adapted to be in fluid communication with the second pair of ancillary lumens 86a, 86b, also shown in FIG. 14A. The second ancillary passageway 81 may be coupled in fluid communication with another tubing section 28 of the delivery tube 14, such as the instrumentation tubing 36 or the multi-lumen tubes 80a, 80b, at a connector port 88b of the split connector 76. Further, an additional tubing section 28 of the delivery tube 14 may be coupled at a connector port 88c of the split connector 76 to provide fluid communication with the primary lumen 82 and the first ancillary lumen 84 through the primary passageway 83 and the first ancillary passageway 78, respectively. When the multi-lumen tubes 80a, 80b are used with the split connector 76, the connector ports 88a, 88b, and 88c may be configured to provide fluid communication with the lumens described above while blocking fluid communication with other lumens.

Figure 18:
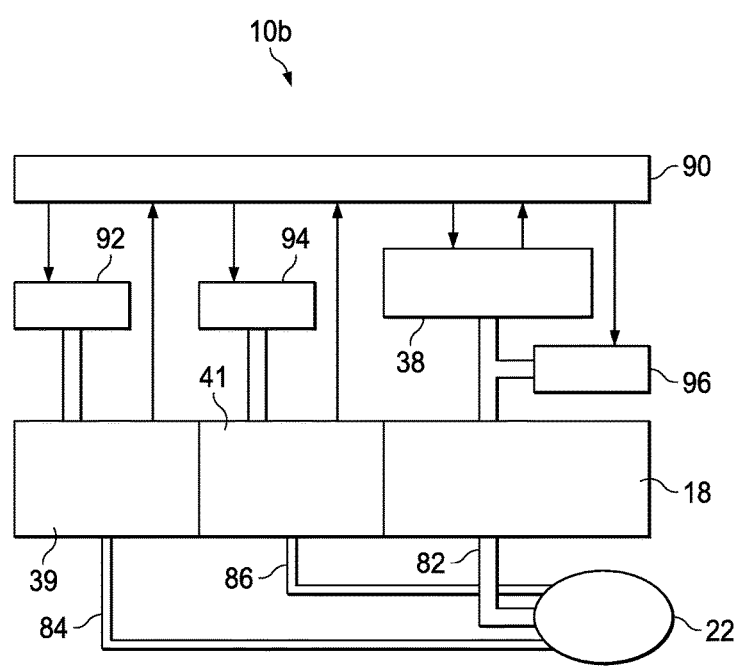
FIG. 18 is a schematic block diagram illustrating a reduced pressure system according to another example embodiment of this disclosure.

FIG. 18 is a schematic diagram illustrating additional details that may be associated with some example embodiments of the RPWT system 10b. FIG. 18 illustrates the reduced pressure source 38, the pressure sensor 39, and the instillation reservoir 41 in separate fluid communication, for example, through separate lumens or conduits, with the adapter 22 as previously described. The RPWT system 10b may additionally include the controller 90, and the solenoid valves 92, 94, and 96. The controller 90 may be configured to receive pressure data from the pressure sensor 39 and the reduced pressure source 38. The controller 90 may also be programmed or configured to monitor pressure at the tissue site 25, shown in FIG. 16, through the pressure data received from the pressure sensor 39. The controller 90 may further be configured to operate the reduced pressure source 38 for supplying reduced pressure to the adapter 22, such as through the previously described primary lumen 82 and primary port 60, according to the pressure data. Additionally, the controller 90 may further be configured to control fluid flow from the instillation reservoir 41 to the adapter 22, such as through the previously described second ancillary lumen 86 and second ancillary port 58.

In some embodiments, the solenoid valve 92 may be in fluid communication with the pressure sensor 39, the solenoid valve 94 may be in fluid communication with the instillation reservoir 41, and the solenoid valve 96 may be in fluid communication with the reduced pressure source 38. The controller 90 may be electrically coupled or operable on the solenoid valves 92, 94, and 96, and the reduced pressure source 38. In the RPWT system 10b, the solenoid valves 92, 94, and 96 may be controlled by the controller 90, for example, to regulate pressure at the tissue site 25 and to clear blockages as described above. Further, the solenoid valve 94 may have various configurations for delivering instillation fluid from the instillation reservoir 41. As shown in FIG. 18, the instillation reservoir 41 may be positioned in fluid communication between the solenoid valve 94 and the second ancillary lumen 86. In such an embodiment, the controller 90 may be operable to open the solenoid valve 94 to atmosphere, thereby releasing vacuum in the instillation reservoir 41, permitting instillation fluid in the instillation reservoir 41 to flow into the second ancillary lumen 86 toward the adapter 22. In other embodiments, the solenoid valve 94 may be positioned in fluid communication between the instillation reservoir 41 and the second ancillary lumen 86 such that opening the solenoid valve 94 may permit instillation fluid to flow from the instillation reservoir 41 by operation of gravity. Other embodiments are possible, and other actuation devices, such as a pump, may be associated with the fluid instillation reservoir 41 to enhance the flow of instillation fluid toward the adapter 22.

Figure 19:
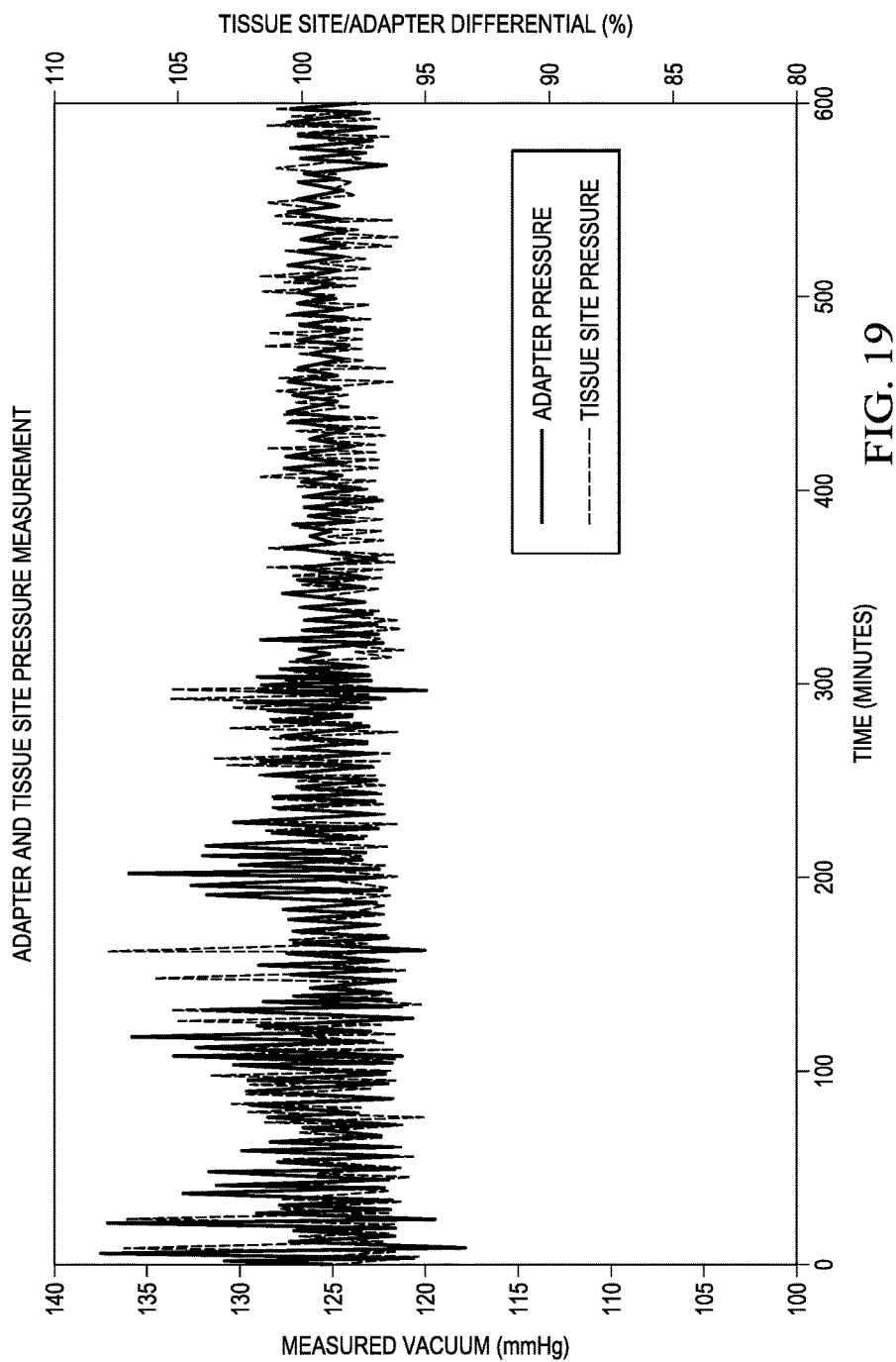
FIG. 19 is a graphical plot of pressure measured at a tissue site by an adapter according to this disclosure compared to a plot of actual pressure present at the tissue site.

Referring to FIG. 19, test results are shown as a graphical plot of pressure measured at a tissue site by embodiments of the adapter 22 including the at least one port extension 37, shown in FIGS. 10-11, compared to a plot of actual pressure present at the tissue site. In FIG. 19, a solid plot line represents the pressure measured by the adapter 22, and a dashed plot line represents the actual pressure measured at the tissue site as a control or baseline. Both the solid and dashed plot lines substantially overlap one another in FIG. 19, indicating that the pressure measured by the adapter 22 provides an accurate representation of the actual pressure at the tissue site.

The use of the at least one port extension 37 may contribute to the accuracy of the pressure measured by the adapter 22. For example, pressure sampling with the port extension 37 occurs at the distal end 45 of the port extension 37, which is adapted to be in contact with or in close proximity to a surface of the tissue site. Sampling pressure through the distal end 45 of the port extension 37, positioned in contact with or in close proximity to the tissue site, may minimize variations in pressure measurements that could occur, for example, due to pressure drops or other losses. Further, the use of the port extension 37 provides additional benefits in regard to efficient use of instillation fluid and improved washing of a tissue site with the instillation fluid. For example, delivering instillation fluid through the distal end 45 of the port extension 37, positioned in contact with or in close proximity to the tissue site, may minimize loss of instillation fluid to other parts of the system, such as, for example, the dressing and the distribution manifold. Thus, the port extension 37 may permit instillation fluid to be delivered directly to a surface of the tissue site without requiring, for example, saturation of the distribution manifold or filling of the wound dressing before the instillation fluid is able to reach a surface of the tissue site.

Figure 20:
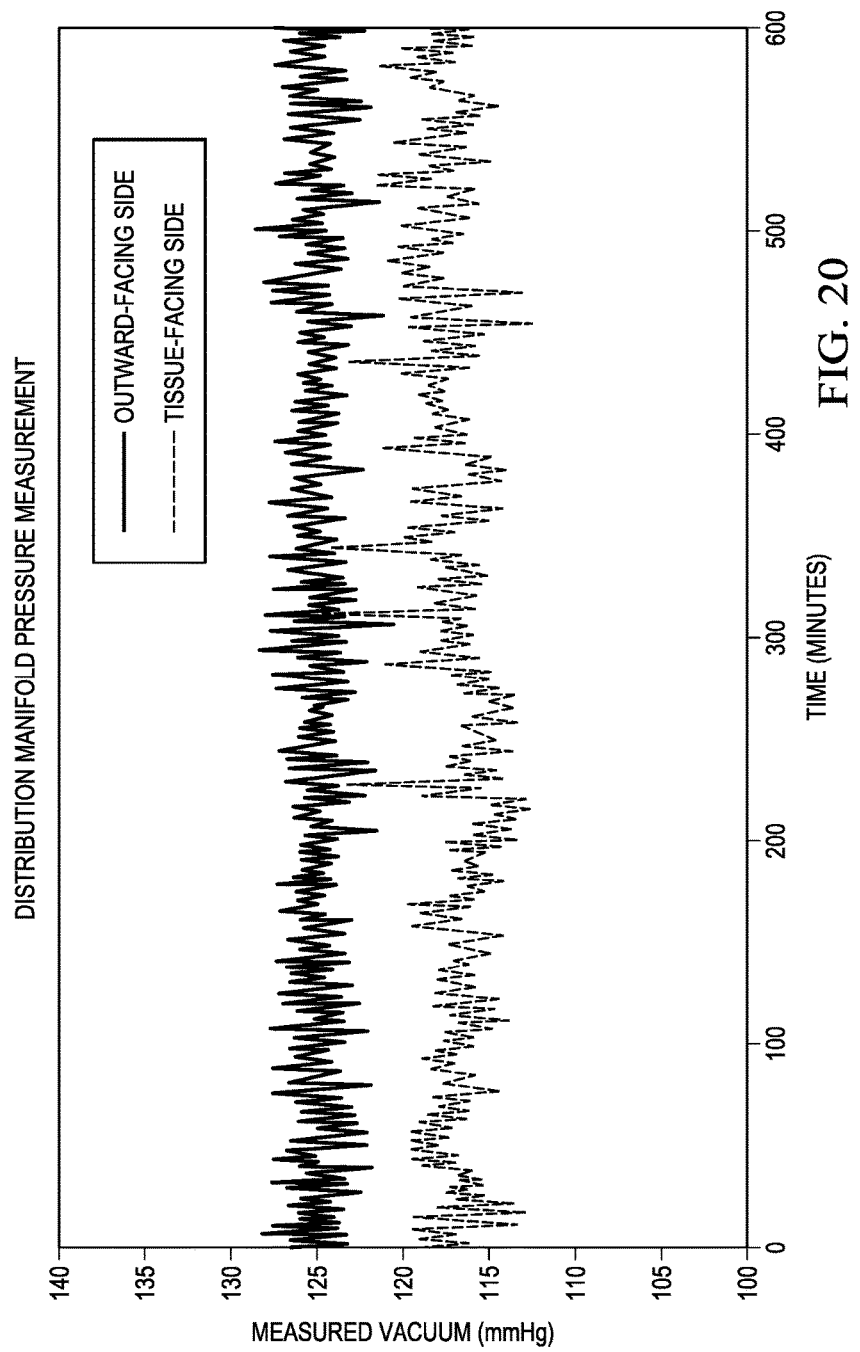
FIG. 20 is a graphical plot of pressure measured at an outward-facing side of a distribution manifold compared to a plot of pressure measured at a tissue-facing side of a distribution manifold according to this disclosure.

Referring to FIG. 20, test results are shown as a graphical plot of pressure measured at an outward-facing side of a distribution manifold by an embodiment of the adapter 22 including a single port extension 37, shown in FIG. 11, compared to a plot of pressure measured at a tissue-facing side of the distribution manifold. In FIG. 20, a solid plot line represents pressure measured at an outward-facing side of the distribution manifold, such as through the second ancillary port 58 of the adapter 22, shown in FIG. 11, which may be adapted to terminate or reside at or on the outward-facing side of the distribution manifold. A dashed plot line in FIG. 20 represents the pressure measured through the adapter 22 and the distal end 45 of the port extension 37, which may be positioned at the tissue-facing side of the distribution manifold and in contact with or in close proximity to the tissue site, providing an accurate representation of the actual pressure at the tissue site as described above. FIG. 20 illustrates a mean pressure difference of about 7 mm Hg between the solid plot line and the dashed plot line, indicating a pressure drop or loss exists across a thickness of the distribution manifold between the outward-facing side and the tissue-facing side. As fluid and particulate exposure from the tissue site to the distribution manifold occurs over time, increases in pressure drop and losses can occur, reducing a life expectancy of the distribution manifold. Thus, the life expectancy of the distribution manifold may be determined by comparing the pressure measured at the outward-facing side of the distribution manifold to the pressure measured at the tissue-facing side of the distribution manifold.

Referring generally to the figures, this disclosure provides methods that may be suitable for use with instillation therapy and reduced-pressure therapy. In some illustrative embodiments, a method for evaluating a service life of a distribution manifold for treating a tissue site may include positioning the distribution manifold 24 on a surface of the tissue site 25. Further, the method may include positioning the adapter 22 including the port extension 37, as shown in FIG. 11, for example, on the distribution manifold 24. In such an embodiment, the distal end 45 of the port extension 37 may extend outward from the entry surface 55 toward the tissue-facing side 61 of the distribution manifold 24, and the second ancillary port 58 may terminate on the entry surface 55 at the outward-facing side 63 of the distribution manifold 24.

Further, the method may include inserting the distal end 45 of the port extension 37 into the distribution manifold 24, and applying reduced pressure to the distribution manifold 24 through the primary port 60 of the adapter 22. Further, the method may include measuring a first pressure between the surface of the tissue site 25 and the tissue-facing side 61 of the distribution manifold 24 through the first ancillary port 56 and the distal end 45 of the port extension 37. Further, the method may include measuring a second pressure at the outward-facing side 63 of the distribution manifold 24 through the second ancillary port 58. Further, the method may include calculating a difference between the first pressure and the second pressure to provide a differential pressure.

In some embodiments, the method may include changing or replacing the distribution manifold 24 if the differential pressure is greater than about 15 mm Hg. Further, in some embodiments, applying reduced pressure may include applying reduced pressure to the outward-facing side 63 of the distribution manifold 24. Further, in some embodiments, the bore 47 of the port extension may define an isolated communication passageway between the distal end 45 of the port extension 37 and the first ancillary port 56. Further, in some embodiments, applying reduced pressure to the distribution manifold 24 may move the outward-facing side 63 of the distribution manifold 24 closer to the surface of the tissue site 25 such that the distal end 45 of the port extension 37 contacts the surface of the tissue site 25. Further, in some embodiments, the method may include covering the outward-facing side 63 of the distribution manifold 24 with the drape 26 to provide a sealed space between the drape 26 and the tissue site 25. The distribution manifold 24 may be positioned in the sealed space.

In other embodiments, a method for evaluating a service life of a distribution manifold for treating a tissue site may include positioning the distribution manifold 24 on a surface of the tissue site 25. Further, the method may include applying reduced pressure to the outward-facing side 63 of the distribution manifold 24. Further, the method may include measuring a first pressure between the surface of the tissue site 25 and the tissue-facing side 61 of the distribution manifold 24. Further, the method may include measuring a second pressure at the outward-facing side 63 of the distribution manifold 24. Further, the method may include calculating a difference between the first pressure and the second pressure to provide a differential pressure.

In some illustrative embodiments, a method for measuring and controlling pressure at a tissue site may include positioning the distribution manifold 24 adjacent a surface of the tissue site 25. The distribution manifold 24 may include a tissue-facing side 61 facing the tissue site 25, and an outward-facing side 63 opposite the tissue-facing side 61. Further, the method may include positioning the adapter 22 adjacent the distribution manifold 24. In such an embodiment, the adapter 22 may include the first ancillary port 56, the second ancillary port 58, the first port extension 37a, and the second port extension 37b as shown in FIG. 10.

Further, the method may include inserting the distal end 45 of the first port extension 37a and the distal end 45 of the second port extension 37b into the distribution manifold 24. Further, the method may include applying reduced pressure from the reduced pressure source 38 to the distribution manifold 24 through the primary port 60. Further, the method may include measuring a first pressure between the tissue-facing side 61 of the distribution manifold 24 and the surface of the tissue site 25 through the first port extension 37a. Further, the method may include measuring a second pressure between the tissue-facing side 61 of the distribution manifold 24 and the surface of the tissue site 25 through the second port extension 37b. Further, the method may include controlling the reduced pressure from the reduced pressure source 38 according to the first pressure and the second pressure.

In other embodiments, a method for measuring and controlling pressure at a tissue site may include positioning the distribution manifold 24 adjacent a surface of the tissue site 25. The distribution manifold 24 may include the tissue-facing side 61 facing the tissue site 25, and an outward-facing side 63 opposite the tissue-facing side 61. Further, the method may include applying reduced pressure from the reduced pressure source 38 to the distribution manifold 24. In some embodiments, applying reduced pressure may include applying reduced pressure to the outward-facing side 63 of the distribution manifold 24. Further, the method may include measuring a first pressure between the surface of the tissue site 25 and the tissue-facing side 61 of the distribution manifold 24. Further, the method may include measuring a second pressure between the surface of the tissue site 25 and the tissue-facing side 61 of the distribution manifold 24. Further, the method may include controlling the reduced pressure from the reduced pressure source 38 according to the first pressure and the second pressure. Further, in some embodiments, the method may include determining a first time period for the first pressure to respond to a change in the reduced pressure at the reduced pressure source 38; determining a second time period for the second pressure to respond to the change in reduced pressure at the reduced pressure source 38; controlling the reduced pressure according to the first time period if the first time period is less than the second time period; and controlling the reduced pressure according to the second time period if the second time period is less than the first time period.

In some illustrative embodiments, a method for instilling fluid at a tissue site may include positioning the distribution manifold 24 adjacent a surface of the tissue site 25. The distribution manifold 24 may include the tissue-facing side 61 facing the tissue site 25, and the outward-facing side 63 opposite the tissue-facing side 61. Further, the method may include positioning the adapter 22 adjacent the distribution manifold 24. In such an embodiment, the adapter 22 may include at least one of the ancillary ports 56, 58, and at least one port extension 37 as shown in FIGS. 10-11. Further, the method may include inserting the distal end 45 of the port extension 37 into the distribution manifold 24, and delivering fluid to the surface of the tissue site 25 through the distal end 45 of the port extension 37.

In some embodiments, the method for instilling fluid may include delivering reduced pressure to the outward-facing side 63 of the distribution manifold 24 through, for example, the primary port 60 of the adapter 22. Further, in some embodiments, the method for instilling fluid may include measuring a pressure between the surface of the tissue site 25 and the tissue-facing side 61 of the distribution manifold 24, and controlling the delivery of reduced pressure according to the pressure.

In other embodiments, a method for instilling fluid at a tissue site may include positioning the distribution manifold 24 adjacent a surface of the tissue site 25. The distribution manifold 24 may include a tissue-facing side 61 facing the tissue site 25, and an outward-facing side 63 opposite the tissue-facing side 61. Further, the method may include delivering fluid directly between the surface of the tissue site 25 and the tissue-facing side 61 of the distribution manifold 24.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations, for example, for purposes of sale, manufacture, assembly, or use. Further, components disclosed in connection with one embodiment may be used in connection with another embodiment.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of this disclosure as defined by the appended claims.

What is claimed is:

1. A system for treating a tissue site, comprising: a distribution manifold comprising a tissue-facing side adapted to face the tissue site and an outward-facing side opposite the tissue-facing side; an adapter for providing fluid communication with the distribution manifold, the adapter comprising: a base including a mounting surface adapted to be positioned on the distribution manifold, a conduit housing supported by the base and including a recessed region defining an entry surface, the entry surface adapted to be positioned fad ng the distribution manifold, a primary port on the entry surface, at least one ancillary port on the entry surface, and at least one port extension including a proximal end, a distal end, and a bore between the proximal end and the distal end, wherein the port extension comprises a sufficient length from the mounting surface and extends into the distribution manifold when the mounting surface is positioned on the distribution manifold, the distal end of the port extension in fluid communication with the ancillary port through the bore; and a reduced pressure source adapted to be positioned in fluid communication with the primary port through the conduit housing.

2. The system of claim 1, wherein the tissue-facing side of the distribution manifold is adapted to contact the tissue site.

3. The system of claim 1, further comprising a drape adapted to cover the outward-facing side of the distribution manifold at the tissue site.

4. The system of claim 1, wherein the length of the port extension is sufficient to extend between the outward-facing side and the tissue-facing side of the distribution manifold.

5. The system of claim 1, wherein the proximal end of the port extension is adapted to be positioned at the outward-facing side of the distribution manifold, and the distal end of the port extension is adapted to be positioned at the tissue-facing side of the distribution manifold.

6. The system of claim 1, wherein the distal end of the port extension is adapted to contact the tissue site.

7. The system of claim 1, wherein the distal end of the port extension carries a plurality of castellations, the castellations spaced apart from one another and extending outward from the distal end of the port extension.

8. The system of claim 1, further comprising a pressure sensor adapted to be positioned in fluid communication with the ancillary port through the conduit housing.

9. The system of claim 1, further comprising an instillation reservoir adapted to hold a liquid and to be positioned in fluid communication with the ancillary port through the conduit housing.

10. The system of claim 1, wherein the at least one ancillary port comprises a first ancillary port and a second ancillary port, the proximal end of the port extension coupled to the entry surface about the first ancillary port, the distal end of the port extension extending outward from the entry surface and beyond the mounting surface of the base, the second ancillary port terminating at the entry surface, the system further comprising:
a first pressure sensor in fluid communication with the first ancillary port through the conduit housing; and
a second pressure sensor in fluid communication with the second ancillary port through the conduit housing.

11. The system of claim 1, wherein the at least one ancillary port comprises a first ancillary port and a second ancillary port, and wherein the at least one port extension comprises a first port extension and a second port extension, the proximal end of the first port extension coupled about the first ancillary port, and the proximal end of the second port extension coupled about the second ancillary port.

12. The system of claim 11, further comprising a first pressure sensor and a second pressure sensor, the first pressure sensor in fluid communication with the first ancillary port, the second pressure sensor in fluid communication with the second ancillary port.

13. The system of claim 11, further comprising a pressure sensor and an instillation reservoir, the pressure sensor in fluid communication with the first ancillary port through the conduit housing, the instillation reservoir in fluid communication with the second ancillary port through the conduit housing.

14. The system of claim 1, the conduit housing further comprising a primary conduit and at least one ancillary conduit, the primary conduit disposed through the conduit housing in fluid communication with the primary port, the ancillary conduit disposed through the conduit housing in fluid communication with the ancillary port.

15. The system of claim 14, further comprising:
a primary lumen adapted to be in fluid communication between the reduced pressure source and the primary conduit; and at least one ancillary lumen adapted to be in fluid communication with the ancillary conduit.

16. The system of claim 1, further comprising:
a primary lumen adapted to be in fluid communication between the reduced pressure source and the primary port; and
at least one ancillary lumen adapted to be in fluid communication with the ancillary port.

17. The system of claim 16, wherein the at least one ancillary port comprises a first ancillary port and a second ancillary port, and wherein the at least one ancillary lumen comprises a first pair of ancillary lumens and a second pair of ancillary lumens, the first pair of ancillary lumens adapted to be in fluid communication with the first ancillary port, the second pair of ancillary lumens adapted to be in fluid communication with second ancillary port.

18. The system of claim 17, wherein the primary lumen, the first pair of ancillary lumens, and the second pair of ancillary lumens form part of a multi-lumen tube.

19. The system of claim 18, further comprising a split connector comprising a first ancillary passageway, a second ancillary passageway, and a primary passageway, the first ancillary passageway adapted to be in fluid communication with the first pair of ancillary lumens, the second ancillary passageway adapted to be in fluid communication with the second pair of ancillary lumens, and the primary passageway adapted to be in fluid communication with the primary lumen.

20. The system of claim 1, wherein the at least one ancillary port comprises a first ancillary port and a second ancillary port, the system further comprising:
a first pressure sensor in fluid communication with the first ancillary port through the conduit housing;
a second pressure sensor in fluid communication with the second ancillary port through the conduit housing; and
a controller configured to receive pressure data from the first pressure sensor, the second pressure sensor, and the reduced pressure source, the controller further configured to operate the reduced pressure source for supplying reduced pressure to the primary port according to the pressure data.

21. The system of claim 1, wherein the at least one ancillary port comprises a first ancillary port and a second ancillary port, the system further comprising:
a pressure sensor in fluid communication with the first ancillary port through the conduit housing;
an instillation reservoir in fluid communication with the second ancillary port through the conduit housing; and
a controller configured to receive pressure data from the pressure sensor and the reduced pressure source, the controller further configured to control fluid flow from the instillation reservoir to the second ancillary port, and to operate the reduced pressure source for supplying reduced pressure to the primary port according to the pressure data.

22. A method for treating a tissue site, comprising:
positioning the distribution manifold on a surface of the tissue site, the distribution manifold comprising a tissue-facing side facing the tissue site and an outward-facing side opposite the tissue-facing side;
positioning an adapter on the distribution manifold, the adapter comprising:
a conduit housing including a recessed region defining an entry surface, the entry surface facing the outward-facing side of the distribution manifold,
a primary port on the entry surface,
a first ancillary port and a second ancillary port on the entry surface, and
a port extension including a proximal end, a distal end, and a bore between the proximal end and the distal end, the distal end of the port extension in fluid communication with the first ancillary port;
inserting the distal end of the port extension into the distribution manifold;
applying reduced pressure to the distribution manifold through the primary port;
measuring a first pressure between the surface of the tissue site and the tissue-facing side of the distribution manifold through the first ancillary port and the distal end of the port extension;
measuring a second pressure at the outward-facing side of the distribution manifold through the second ancillary port; and
calculating a difference between the first pressure and the second pressure to provide a differential pressure.

23. The method of claim 22, further comprising changing the distribution manifold if the differential pressure is greater than 15 mm Hg.

24. The method of claim 22, wherein the distal end of the port extension extends outward from the entry surface toward the tissue-facing side of the distribution manifold and the second ancillary port terminates on the entry surface at the outward-facing side of the distribution manifold.

25. The method of claim 22, wherein applying reduced pressure comprises applying reduced pressure to the outward-facing side of the distribution manifold.

26. The method of claim 22, wherein the bore defines an isolated communication passageway between the distal end of the port extension and the first ancillary port.

27. The method of claim 22, wherein applying reduced pressure to the distribution manifold moves the outward-facing side of the distribution manifold closer to the surface of the tissue site such that the distal end of the port extension contacts the surface of the tissue site.

28. The method of claim 22, further comprising covering the outward-facing side of the distribution manifold with a drape to provide a sealed space between the drape and the tissue site, the distribution manifold positioned in the sealed space.

29. A method for instilling fluid at a tissue site, comprising:
positioning a distribution manifold adjacent a surface of the tissue site, the distribution manifold comprising a tissue-facing side facing the tissue site and an outward-facing side opposite the tissue-facing side;
positioning an adapter adjacent the distribution manifold, the adapter comprising:
a conduit housing including a recessed region defining an entry surface, the entry surface facing the outward-facing side of the distribution manifold,
a primary port on the entry surface,
at least one ancillary port on the entry surface, and
at least one port extension including a proximal end, a distal end, and a bore between the proximal end and the distal end, the distal end of the port extension in fluid communication with the ancillary port through the bore;
inserting the distal end of the port extension into the distribution manifold; and
delivering fluid to the surface of the tissue site through the ancillary port and the distal end of the port extension.

30. The method of claim 29, further comprising delivering reduced pressure to the outward-facing side of the distribution manifold through the primary port.

31. The method of claim 30, further comprising measuring a pressure between the surface of the tissue site and the tissue-facing side of the distribution manifold, and controlling the delivery of reduced pressure according to the pressure.

* * * * *